(12) United States Patent
Van Dyke et al.

(10) Patent No.: US 9,220,754 B2
(45) Date of Patent: Dec. 29, 2015

(54) KERATIN COMPOSITIONS FOR TREATMENT OF BONE DEFICIENCY OR INJURY

(71) Applicant: Wake Forest University Health Sciences, Winston-Salem, NC (US)

(72) Inventors: Mark E. Van Dyke, Winston-Salem, NC (US); Thaleia Teli, Athens (GR)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 13/895,485

(22) Filed: May 16, 2013

(65) Prior Publication Data

US 2013/0251689 A1 Sep. 26, 2013

Related U.S. Application Data

(63) Continuation of application No. PCT/US2011/061190, filed on Nov. 17, 2011.

(60) Provisional application No. 61/414,748, filed on Nov. 17, 2010.

(51) Int. Cl.
| | |
|---|---|
| A61K 38/17 | (2006.01) |
| A61K 38/18 | (2006.01) |
| A61K 35/28 | (2015.01) |
| A61K 38/39 | (2006.01) |
| A61L 27/22 | (2006.01) |
| A61L 27/44 | (2006.01) |
| A61L 27/54 | (2006.01) |
| A61K 45/06 | (2006.01) |

(52) U.S. Cl.
CPC .............. *A61K 38/1748* (2013.01); *A61K 35/28* (2013.01); *A61K 38/1875* (2013.01); *A61K 38/39* (2013.01); *A61K 45/06* (2013.01); *A61L 27/227* (2013.01); *A61L 27/44* (2013.01); *A61L 27/54* (2013.01); *A61L 2300/406* (2013.01); *A61L 2430/02* (2013.01)

(58) Field of Classification Search
CPC ........... A61K 38/1748; A61K 38/1875; A61K 35/28; A61K 38/39; A61L 2430/39
See application file for complete search history.

(56) References Cited

U.S. PATENT DOCUMENTS

| | | |
|---|---|---|
| 922,692 A | 5/1909 | Goldsmith |
| 926,999 A | 7/1909 | Neuberg |
| 960,914 A | 6/1910 | Heinemann |
| 1,214,299 A | 1/1917 | Grosvenor et al. |
| 2,434,688 A | 1/1948 | Evans |
| 2,445,028 A | 7/1948 | Jones et al. |
| 2,517,572 A | 8/1950 | Jones et al. |
| 2,814,851 A | 12/1957 | Hervey |
| 3,033,755 A | 5/1962 | Jacobi |
| 3,642,498 A | 2/1972 | Anker |
| 3,655,416 A | 4/1972 | Vinson et al. |
| 4,178,361 A | 12/1979 | Cohen et al. |
| 4,357,274 A | 11/1982 | Werner et al. |
| 4,423,032 A | 12/1983 | Abe et al. |
| 4,495,173 A | 1/1985 | Matsunaga et al. |
| 4,570,629 A | 2/1986 | Widra |
| 4,751,074 A | 6/1988 | Matsunaga et al. |
| 4,774,227 A | 9/1988 | Piez et al. |
| 4,795,467 A | 1/1989 | Piez et al. |
| 4,865,602 A | 9/1989 | Smestad et al. |
| 4,895,722 A | 1/1990 | Abe et al. |
| 4,959,213 A | 9/1990 | Brod et al. |
| 5,047,249 A | 9/1991 | Rothman et al. |
| 5,300,285 A | 4/1994 | Halloran et al. |
| 5,320,796 A | 6/1994 | Harashima et al. |
| 5,358,935 A | 10/1994 | Smith et al. |
| 5,634,945 A | 6/1997 | Pernia et al. |
| 5,636,643 A | 6/1997 | Argenta et al. |
| 5,645,081 A | 7/1997 | Argenta et al. |
| 5,651,966 A | 7/1997 | Read et al. |
| 5,679,819 A | 10/1997 | Jones et al. |
| 5,763,583 A | 6/1998 | Arai et al. |
| 5,883,078 A | 3/1999 | Seelich et al. |
| 5,902,608 A | 5/1999 | Read et al. |
| 5,932,552 A | 8/1999 | Blanchard et al. |
| 5,948,432 A | 9/1999 | Timmons et al. |
| 6,110,487 A | 8/2000 | Timmons et al. |
| 6,124,265 A | 9/2000 | Timmons et al. |
| 6,159,495 A | 12/2000 | Timmons et al. |

(Continued)

FOREIGN PATENT DOCUMENTS

| | | |
|---|---|---|
| DE | 184915 | 12/1905 |
| DE | 22643 | 10/1907 |

(Continued)

OTHER PUBLICATIONS

Gillis, J.N.; et al; "Selective retention of oxygen using chromatographic columns containing metal chelate polymers."; Analytical Chemistry; vol. 57(8), 1985, pp. 1572-1577.

Gough, K.H. et al; "Amino acid sequences of alpha-helical segments from S-carboxymethylkerateine-A. Complete sequence of a type—I segment."; Biochemical Journal; vol. 173 (2), 1978, pp. 373-385.

Green, M.R.; Basketter, D.A.; Couchman, J.R.; Rees, D.A.; "Distribution and number of epidermal growth factor receptors in skin is related to epithelial cell growth.;" Developmental Biology; vol. 100, 1983, pp. 506-512.

(Continued)

*Primary Examiner* — Allison Fox
(74) *Attorney, Agent, or Firm* — Myers Bigel Sibley & Sajovec, P.A.

(57) ABSTRACT

A bone graft composition is described, with one or more of: (a) keratose; (b) kerateine; (c) optionally, particulate filler; (d) optionally, an antibiotic; and (e) water or saline. The composition may be provided in sterile form in a container, and optionally lyophilized. Methods of treating a bone deficiency or fracture making use of such compositions are also described.

30 Claims, 4 Drawing Sheets

(56) References Cited

U.S. PATENT DOCUMENTS

| | | | |
|---|---|---|---|
| 6,159,496 | A | 12/2000 | Blanchard et al. |
| 6,165,496 | A | 12/2000 | Timmons et al. |
| 6,268,454 | B1 | 7/2001 | Song et al. |
| 6,270,791 | B1 | 8/2001 | Van Dyke et al. |
| 6,270,793 | B1 | 8/2001 | Van Dyke et al. |
| 6,274,155 | B1 | 8/2001 | Van Dyke et al. |
| 6,274,163 | B1 | 8/2001 | Blanchard et al. |
| 6,309,422 | B1 | 10/2001 | Farrington et al. |
| 6,316,598 | B1 | 11/2001 | Van Dyke et al. |
| 6,371,984 | B1 | 4/2002 | Van Dyke et al. |
| 6,379,690 | B2 | 4/2002 | Blanchard et al. |
| 6,432,435 | B1 | 8/2002 | Timmons et al. |
| 6,461,628 | B1 | 10/2002 | Blanchard et al. |
| 6,544,548 | B1 | 4/2003 | Siller-Jackson et al. |
| 6,696,073 | B2 | 2/2004 | Boyce et al. |
| 6,746,836 | B1 | 6/2004 | Widra |
| 6,783,546 | B2 | 8/2004 | Zucherman et al. |
| 6,825,323 | B2 | 11/2004 | Hess |
| 6,833,488 | B2 | 12/2004 | Bucevschi et al. |
| 6,869,445 | B1 | 3/2005 | Johnson |
| 7,297,342 | B2 | 11/2007 | Peplow et al. |
| 7,439,012 | B2 | 10/2008 | Van Dyke |
| 7,892,572 | B2 | 2/2011 | Peplow et al. |
| 7,892,573 | B2 | 2/2011 | Van Dyke |
| 8,299,013 | B2 | 10/2012 | Van Dyke |
| 2002/0192196 | A1 | 12/2002 | Allen-Hoffmann |
| 2003/0109587 | A1 | 6/2003 | Mori |
| 2003/0228353 | A1 | 12/2003 | Cowsar |
| 2004/0062793 | A1 | 4/2004 | Dyke |
| 2004/0078090 | A1 | 4/2004 | Binette et al. |
| 2004/0120910 | A1 | 6/2004 | Dyke |
| 2004/0267362 | A1 | 12/2004 | Hwang et al. |
| 2005/0084542 | A1 | 4/2005 | Rosenberg et al. |
| 2007/0166348 | A1 | 7/2007 | Van Dyke |
| 2008/0039951 | A1 | 2/2008 | Peplow et al. |
| 2008/0213228 | A1 | 9/2008 | Edinger et al. |
| 2008/0274165 | A1 | 11/2008 | Van Dyke |
| 2009/0004242 | A1 | 1/2009 | Van Dyke |
| 2009/0017001 | A1 | 1/2009 | Van Dyke |
| 2009/0047260 | A1 | 2/2009 | Van Dyke |

FOREIGN PATENT DOCUMENTS

| | | |
|---|---|---|
| EP | 0089152 A1 | 9/1983 |
| EP | 0 454 600 | 10/1991 |
| EP | 0468797 A2 | 1/1992 |
| EP | 0 540 357 A2 | 5/1993 |
| GB | 531446 A | 1/1941 |
| GB | 2 241 253 A | 8/1991 |
| JP | 52-148581 A | 12/1977 |
| JP | 53-016091 A | 2/1978 |
| JP | 54-137064 A | 10/1979 |
| JP | 55-051095 A | 4/1980 |
| JP | 56-030909 A | 3/1981 |
| JP | SHO 55-98256 | 2/1982 |
| JP | S57-109797 | 7/1982 |
| JP | 60-122568 A | 7/1985 |
| JP | 1-174528 | 7/1989 |
| JP | 2-051533 A | 2/1990 |
| JP | 3-011099 A | 1/1991 |
| JP | 4-082561 A | 3/1992 |
| JP | 4-091138 A | 3/1992 |
| JP | HEI 4-189833 | 7/1992 |
| JP | 5-285374 A | 11/1993 |
| JP | 5-285375 A | 11/1993 |
| JP | 5-320358 A | 12/1993 |
| JP | 6-100600 A | 4/1994 |
| JP | 6-116300 A | 4/1994 |
| JP | 6-336499 A | 12/1994 |
| JP | 8332087 A | 12/1996 |
| JP | 9-227565 A | 9/1997 |
| JP | 10-291998 A | 11/1998 |
| JP | 10-291999 A | 11/1998 |
| JP | 10-337466 | 12/1998 |
| JP | 2000-191792 A | 7/2000 |
| JP | 2001-087754 A | 4/2001 |
| JP | 2001-114647 A | 4/2001 |
| JP | 2001329183 A | 11/2001 |
| JP | 2004136096 A | 5/2004 |
| NL | 51000577 | 12/1941 |
| RU | 2 106 154 C1 | 3/1998 |
| RU | 2 108 079 C1 | 4/1998 |
| WO | WO 91-02538 A1 | 3/1991 |
| WO | WO 93/10827 A1 | 6/1993 |
| WO | WO 93/12819 A1 | 7/1993 |
| WO | WO 98/08550 A1 | 3/1998 |
| WO | WO 99/26570 A1 | 6/1999 |
| WO | WO 99/26595 A1 | 6/1999 |
| WO | WO 99/51175 A1 | 10/1999 |
| WO | WO 00/76437 A1 | 12/2000 |
| WO | WO 01/19283 A2 | 3/2001 |
| WO | WO 01/19305 A1 | 3/2001 |
| WO | WO 01/64033 A2 | 9/2001 |
| WO | WO 02/45508 A1 | 6/2002 |
| WO | WO 03/011894 A1 | 2/2003 |
| WO | WO 03/064449 A2 | 8/2003 |
| WO | WO 03/086491 A2 | 10/2003 |
| WO | WO 2004/091432 A2 | 10/2004 |
| WO | WO 2007/098053 | 8/2007 |
| WO | WO 2007/098114 A2 | 8/2007 |
| WO | WO 2008/130607 A2 | 10/2008 |
| WO | WO 2012/068376 A2 | 5/2012 |

OTHER PUBLICATIONS

Greven, R.; et al.; "Morphological origin of the S-carboxymethyl kerateines of wool."; Textile Research Journal vol. 56; 1986, pp. 523-526.

Grotendorst, G.R.; et al.; "Novel transforming growth factor β response element controls the expression of the connective tissue growth factor gene."; Cell Growth and Differentiation; vol. 7, 1996, pp. 469-480.

Han, C.H.; et al; "Effect of glycerol addition on the structure and properties of soluble wool keratose films."; Journal of the Korean Fiber Society; vol. 37,No. 8, 2000, pp. 442-447.

Hanukoglu, I.; et al.; "The cDNA sequence of a human epidermal keratin: Divergence of the sequence but conservation of structure among intermediate filament proteins." Cell; vol. 31, 1982, pp. 243-252.

Happey, F.; "Polycrystralline structure of wool." Nature; No. 4218, 1950, pp. 397-398.

Happey, F.; Wormell, R. L.; "Regenerated keratin fibers from wool." Journal Textile Inst.; vol. 40, 1949, pp. T855-T869.

Happey, F.; Wormell, R. L.; "Regenerated keratin fibers."; Nature ; vol. 163, 1949, p. 18.

Harding, H.W.J.; et al; "Enzymic conversion of arginine to citrulline in a hair protein precursor.", Proceedings of the Australian Biochemical Society; ; vol. 9, 1976, pp. 18.

Harding, H.W.J.; Rogers, G.E.; "Formation of ϵ(γ-Glutamyl) lysine cross-link in hair proteins. Investigation of transamidases in hair follicles." The Journal of Biochemistry; vol. 11, No. 15, 1972 pp. 2858-2863.

Hardy, M.H.; "The Secret life of the hair follicle."; Trends in Genetics; vol. 8, No. 2, 1992, pp. 55-60.

Harrap, B.S.; et al; "Soluble derivatives of feather keratin. (I) Isolation, fractionation and amiino acid composition." Biochemistry Journal; vol. 92, 1964, pp. 8-18.

Harris, M.; et al.; "Testing for oxidation damage of wool by alkali solubility." The Textile Manufacturer; vol. 63, 1937, pp. 36,37.

Hewish, D.R.; et al; "In vitro growth and differentiation of epithelial cells derived from post-embryonic hair follicles."; Australian Journal of Biological Sciences; vol. 35, No. 1, 1982, pp. 103-109.

Hiroshi, S.; et al; "Differential Thermal Analysis of component proteins from wool." Institute for Chemical Research, Kyoto University, Uji, Kyoto; vol. 38, 1982, pp. 517-522.

Hogg, D.M.; et al; "Amino acid sequences of alpha-helical segments from S-carboxymethylkerateine-A. Tryptic and chymotryptic peptides from a type II segment."; Biochemical Journal; vol. 173(2), 1978, pp. 353-363.

(56) References Cited

OTHER PUBLICATIONS

Horn, J.C.; Speakman, P.T.; "Relative molecular masses of reduced wool keratin polypeptides" Biochemistry Society Transcript, vol. 14, 1986, pp. 333, 334.
Hu, J.; et al; "Preparation of stable solution of keratin from human hair and structure and properties of the cast film."; Gaofenzi Cailiao Kexue Yu Gongcheng; vol. 18 (2), 2002, pp. 131-133.
Humphries, M.; "Protein-silicone copolymers."; Cosmetics News; vol. 16, No. 92, 1993, pp. 313-318.
Hynd, P.I.; et al; "Amino acid transport in wool and hair follicles."; Experimental Dermatology; vol. 8, 1999, pp. 325-326.
Hübner, G.; et al.; "Strong induction of activin expression after injury suggests an important role of activin in wound repair."; Developmental Biology; vol. 173, 1996, pp. 490-498.
Igarashi, A.; et al.; "Regulation of connective tissue growth factor gene expression in human skin fibroblasts and during wound repair." Molecular Biology of the Cell; vol. 4, 1993, pp. 637-645.
Ikkai, F.; et al; "Dynamic light scattering and circular dichroism studies on heat-induced gelation of hard-keratin protein aqueous solutions."; Biomacromolecules, vol. 3, No. 3, 2002, pp. 482-487.
Ito, H.; et al; "Biocompatability of denatured keratins from wool."; Kobunshi Ronbunshu; vol. 39(4), 1982, pp. 249-256.
Iwatsuki, K.; Viac, J.; Reano, A; Morera, A; Staquet, M.J.; Thivolet, J.; Monier, J.C.; "Comparative studies on the naturally ocurring antikeratin antibodies in human sera."; The Journal of Investigative Dermatology; vol. 87, No. 2, 1986, pp. 179-184.
Jahoda, C.A.B.; et al.; "Dermal-Epidermal Interactions: Adult Follicle-derived cell populations and hair growth."; Dermatologic Clinics; vol. 14, No. 4 1996, pp. 573-583.
Jenkins, B.J. ; et al; "Isolation and characterization of a sheep cysteine-rich cuticle keratin pseudogene."; DNA Sequence; vol. 3, 1992, pp. 181-184.
Jenkins, B.J. et al; "Differential expression of genes encoding a cysteine-rich keratin in the hair cuticle."; Journal of Investigative Dermatology; vol. 103, 1994, pp. 310-317.
Jezowska-Trezebiatowska, B.; et al; "New cobalt (II) complexes, reversibly binding oxygen in aqueous solution."; Bulletin de l'Academie Polonaise des Sciences, Serie des Sciences Chimiques; vol. 20 (3), 1972, pp. 187-192.
Johnson, P.C.; et al; "Oxidative metabolism and blood flow regulation: The search for the missing link."; Journal of Vascular Research; vol. 37 (1) 2000, pp. 83.
Jones, C.M.; et al.; "Involvement of Bone Morphogenetic Protein-4 (BMP-4) and Vgr-1 in morphogenesis and neurogenesis in the mouse."; Development; vol. 111, 1991, pp. 531-542.
Jones, L.N.; "Studies on Microfibrils from alpha-Keratin."; Biochimica et Biophysica Acta ; vol. 446. 1976, pp. 515-524.
Jones, L.N.; et al; "Studies of developing human hair shaft cells in vitro."; Journal of Investigative Dermatology; vol. 90, No. 1, 1988, pp. 58-64.
Jozefowicz, M.; Jozefonvicz, J; "Functional Polymers and Cells"; Biomaterials; vol. 16, No. 4, 1988, pp. 831-870.
Katoh, K.; et al; "Multi-functionalization of fiber made of natural polymer."; Aichi-ken Sangayo Gijutsu Kenkyusho Kenkyu Hokoku; vol. 1, 2002, pp. 174-177.
Katsuumi, K.; Ito, M; Kazama, T.; Sato, Y.; "Two dimensional electrophoretic analysis of human hair keratins, especially hair matrix proteins." Archives of Dermatological Research; vol. 281, 1989, pp. 495-501.
Kawano, Y.; et al; "Film and gel of keratins."; Kagaku To Seibutsu; vol. 13 (5), 1975, pp. 291-292.
Kemp, D.J. et al; "Differentiation of avian keratinocytes. Characterization and relationships of the keratin proteins of adult and embryonic feathers and scales."; Biochemistry; vol. 11, No. 6, 1972, pp. 969-975.
Kemp, D.J.; Rodgers, G.E.; "Immunological and immunofluorescent studies on keratin of the hair follicle."; Journal of Cell Science; vol. 7, 1970, pp. 273-283.

Kikkawa, M.; et al; "Solubilization of keratin. Solubilization of feather keratin by oxidation with performic acid."; Hikaku Kagaku,(Leather Chemistry) vol. 20(3), 1974, pp. 151-162.
Klement, V.; et al; "The use of computer-analysis for the quantification of 2-D electrophoretic hair keratin patterns—a pilot study."; Journal of the Forensic Science Society; vol. 24, No. 4, 1984, pp. 440.
Koga, J. et al.; "FTIR study on structural transformation of keratin films induced by stretching."; Journal of Applied polymer Science; vol. 37, 1989, pp. 2131-2140.
Kothapalli, D.; et al.; "Transforming growth factor β induces anchorage-independent growth of NRK fibroblast via a connective tissue growth factor-dependent signaling pathway." Cell Growth and Differentiation; vol. 8, 1997, pp. 61-68.
Kowalska, K.; et al; "New bacterial peptides isolated from structural proteins (keratin of porcine bristle)."; Peptides; Proceedings of the European Peptide Symposium, 25th, 1998, pp. 792-793.
Kozlowski, H.; et al; "Nickel (II) complexes with sulfhydryl containing pepetides. Potentiometric and spectroscopic studies."; Journal of Inorganic Biochemistry; vol. 29 (3), 1987, pp. 187-197.
Kuczek, E.S.; et al; "Sheep wool (glycine+tyrosine)-rich keratin genes: a family of low sequence homology."; European Journal of Biochemistry; vol. 166, 1987, pp. 79-85.
Kulkarni, V.G.; "Further studies on the microfibrils from wool keratin. Part I: the isolation of microfibrils."; Textile Research Journal; vol. 46, No. 11, 1976, pp. 833-835.
Kurimoto, A.; et al.; "Conjugation of keratin sponge with bioactive substances utilizing free cysteine residues. Conjugation of lysozyme."; Nippon Kagakkai Koen Yokoshu; vol. 7, No. 2, 2001, pp. 818.
Kvedar, J.C.; et al.; "Cytokeratins of the bovine hoof : classification and studies on expression."; Biochimica et Biophysica Acta; vol. 884, 1986, pp. 462-473.
Lambre, C.R.; Alaoui-Slimani, N.; Bignon, J.; "An enzyme immunoassay for the auto-antibodies to keratin in normal human serum and in pleural fluids from patients with various malignant or non-malignant lung diseases."; Journal of Clinical and Laboratory Immunology; vol. 20, 1986, pp. 171-176.
Laplaza, C.E.; et al; "Helix-loop-helix-peptide as scaffolds for the construction of bridged metal assemblies in proteins: The spectroscopic A—cluster structure in carbon monoxide dehydrogenase."; Journal of the American Chemical Society, vol. 123, (42), 2001, pp. 10255-10264.
Lee, K.Y.; "Characterization of Silk Fibroin/S-carboxymethyl keratein surfaces: Evaluation of the biocompatibility by contact angle measurement."; Fibers and Polymers; vol. 2, No. 2, 2001, pp. 71-74.
Leeder, J.D.; et al; "Readily extracted proteins from Merino wool."; Textile Research Journal; vol. 52, No. 4, 1982, pp. 245-249.
Lennox, F.G.; "Protein fibers. Chemistry."; Review of Textile Progress Journal; vol. 17, 1967, pp. 81-97.
Lennox, F.G.; et al.; "Photochemical degradation of keratins."; Photochemistry and Photobiology; vol. 9, No. 4, 1969, pp. 359-367.
Leon, N.H.; "The chemical reactivity and modification of keratin fibres." Textile Progress vol. 7, No. 1975, pp. 1-81.
Letter,J.E.; Jordan,R.B.; "Complexing of Nickel(II) by cysteine, tyrosine and related ligands and evidence for zwitterion reactivity." Journal of the American Chemical Society; vol. 9, No. 97, 1975, pp. 2381-2390.
Ley, K.; et al; "Release of cuticle from wool by agitation in solutions of detergents."; Australian Journal of Biological Sciences; vol. 41, No. 2, 1988, pp. 163-176.
Ley, K.F.; et al; "Wool cuticle—new approaches to its production and protein characterization."; Proceedings of the Australian Biochemical Society; vol. 14, 1981, pp. 14.
Li, C-X.; et al; "Purification of natural antikeratin autoantibodies from natural human serum and their effect on human keratinocytes cultured in vivo."; British Journal of Dermatology; vol. 145, No. 5, 2001, pp. 737-748.
Lindley, H. et al.; "High-sulfur protein fractions of keratins."; *Applied Polymers Symposium*; vol. 18, No. 1, 1971, pp. 21-35.
Lindley, H.; et al; "The occurance of the Cys-Cys sequence in keratins."; Journal of Molecular Biology; vol. 30, No. 1, 1967, pp. 63-67.

(56) References Cited

OTHER PUBLICATIONS

Lindley, H.; et al; "The preparation and properties of a group of proteins from the high sulphur fraction of wool"; Biochemical Journal; vol. 128, No. 4, 1972, pp. 859-867.

Lindley, H.; et al; "The reactivity of the disulphide bonds of wool"; Biochemical Journal; vol. 139, No. 3, 1974, pp. 515-523.

Lindley,, H.; et al; "Disulphide interchange reactions involving cyclosystine and their relevance to problems of α-keratin structure" Biochemical Journal; vol. 108, No. 4, 1968, pp. 701-703.

Lissizin, Th.; "Behavior of keratin sulfur and cystin sulfur, in the oxidation of these proteins by potassium permanganate." Biochemistry Bulletin vol. 4, 1915, pp. 18-23.

Lissizin, Th.; "The oxidation products of keratin by oxidation with permanganate." Z. Physiology Chem. vol. 173, 1928, pp. 309-311.

Liu, S.M.; et al; "Transsulfuration, protein synthesis rate and follicle mRNA in the skin of young Merino lambs in response to infusions of methionine and serine."; British Journal of Nutrition; vol. 83, No. 4, 2000, pp. 401-409.

Lotay, S.S.; Speakman, P.T.; "Three-chain merokeratin from wool may be a fragment of the microfibril component macromolecule"; Nature; vol. 265, 1977, pp. 274-277.

Lyons, K.M.; et al.; "Patterns of expression of murine Vgr-1 and BMP-2a RNA suggest that transforming growth factor-β-like genes coordinately regulate aspects of embryonic development." Genes & Development; vol. 3, 1989, pp. 1657-1668.

Mack, J.W.; Torchia, D.A.; Steinert, P.M.; "Solid-State NMR Studies of the Dynamics and Structure of Mouse Keratin Intermediate Filaments."; Biochemistry; vol. 27, No. 15. 1988, pp. 5418-5426.

MacKinnon, P.J.; et al; "An ultrahigh-sulphur keratin gene of the human hair cuticle is located at 11q13 and cross-hybridizes with sequences at 11p15."; Mammalian Genome; vol. 1, 1991 pp. 53-56.

MacLaren, J.A.; "The extent of reduction of wool proteins by thiols." The Australian Journal of Chemistry; vol. 15,No. 4, 1962, pp. 824-831.

Marikovsky, M.; et al.; "Appearance of heparin-binding EGF-like growth factor in wound fluid as a response to injury."; Proceedings of the National Academy of Sciences, USA; vol. 90, 1993, pp. 3889-3893.

Marshall, R.C. et al; "High-sulfur proteins in mammalian keratins: a possible aid in classification."; Australian Journal of Zoology; vol. 25, No. 1, 1977, pp. 121-132.

Marshall, R.C.; "Successful isoelectric-focusing of wool low-sulphur proteins.";Journal of Chromatography; vol. 172, 1979, pp. 351-356.

Marshall, R.C.; "Analysis of the proteins from single wool fibers by two-dimensional polyacrylamide-gel electrophoresis."; Textile Research Journal; vol. 51, No. 2, 1981, pp. 106-108.

Marshall, R.C.; "Changes in wool low-sulphur and high-sulphur protein-components following chemical defleecing."; Textile Research Journal; vol. 51, No. 6, 1981, pp. 384-388.

Marshall, R.C.; "Characterization of the proteins of human hair and nail by electrophoresis."; Journal of Investigative Dermatology; vol. 80, No. 6, 1983, pp. 519-524.

Marshall, R.C.; "Cysteine-rich proteins of mouse hair"; Proceedings of the Australian Biochemical Society; vol. 8, 1975, pp. 4.

Marshall, R.C.; "Forensic identification of hairs by electrophoresis."; Journal of the Forensic Society; vol. 24, No. 4, 1984, pp. 340.

Marshall, R.C.; "Genetic variation in the proteins of human nail."; Journal of Investigative Dermatology; vol. 75, No. 3, 1980, pp. 264-269.

Marshall, R.C.; et al; "An investigation of the relationship of wool textile properties to fiber protein composition."; Proceedings of the International Wool Textile Research Conf.; vol. 1, 1990, pp. 266-275.

Marshall, R.C.; et al; "Examination of proteins of wool cuticle by two-dimensional gel-electrophoresis."; Textile Research Journal; vol. 56, No. 12, 1986, pp. 772-774.

Sizin, T.L.; "The occurance of azelaic acid among the oxidation products of keratin." Z. Physiology Chemistry: vol. 62, 1910, pp. 226-228.

Skerrow, D.; Skerrow, C.J.; Hunter, I.; "Epidermal alpha-keratin is neutral-buffer-soluable and forms intermediate filaments under physiological conditions in vitro."; Biochimica et Biophysica Acta; vol. 915. 1987, pp. 125-131.

Smith, A.L.; et al; "Oxidation of Wool—The Effect of Hydrogen Peroxide." Rayon Textile Monthly; vol. 39, 1936. pp. 39,40.

Smith, A.L.; et al; "Oxidation of Wool: The lead acetate test for hydrogen peroxide bleached wool." Journal of Research of the National Bureau of Standards, vol. 16, 1936, pp. 309-312.

Sparrow, L.G.; et al; "Further resolution of the low sulphur S-carboxymethylkerateine fraction from wool by acrylamide-gel electrophoresis."; Journal of Textile Institute; vol. 63, No. 11, 1972, pp. 619-621.

Starger, J.M.; Brown, W.E.; Goldman, A.E.; Goldman, R.D.; "Biochemical and immunological analysis of rapidly purified 10-nm filaments from baby hamster kidney (BHK-21) cells." The Journal of Cell Biology, vol. 78, 1978, pp. 93-109.

Stary, Z.; "Brominated keratin and oxykeratin."; Z. Physiology Chemistry; vol. 144, 1925, pp. 147-177.

Stary, Z.; "Solubility and digestibility of the degradation products of albumoids." Z. Physiology Chemistry; vol. 136, 1924, pp. 160-172.

Steinert, P.M.; et al; "In vitro studies on the synthesis of guinea pig hair keratin proteins." Biochimica et Biophysica Acta; vol. 312, 1973, pp. 403-412.

Stenn, K.S.; "The molecular and structural biology of hair, Introduction."; Annals of New York Academy of Sciences; vol. 83, 1959, pp. 359-512.

Stenn, K.S.; et al.; "Controls of hair Follicle cycling . . . "; Physiological Reviews; vol. 81, No. 1, 2001, pp. 449-494.

Stenn, K.S.; et al.; "Hair follicle growth controls." Dermatologic Clinics; vol. 14, No. 4, 1996, pp. 543-558.

Stenn, K.S.; et al.; "Molecules of the cycling hair follicle—a tabulated review." Journal of Dermatalogical Science 7(Suppl.) 1994, pp. 109-124.

Stephenson, N.A.; et al; "Preparation and dioxygen binding properties of a new cobalt (II) complex and the crystal structure of the corresponding copper (II) adduct."; Journal of the Chemical Society, Dalton Transactions: Inorganic Chemistry, 150th Anniv. Celebration issue, 1991, pp. 733-738.

Stokes,G.D.; Dunson, W.A.; "Passage of water and electrolytes through natural and artificial keratin membranes." Desalination; vol. 42, 1982, pp. 321-328.

Struessmann, A.; et al.; "Specific radiolabeling of keratin proteins by amidination."; Journal of Chromatography, vol. 268, 1983, pp. 306-310.

Suzuki, E.; et al; "X-ray diffraction and infrared studies of an α-helical fragment from α-keratin." Journal of Molecular Biology; vol. 73, 1973, pp. 275-278.

Tachibana, A. et al.; "Fabrication of wool keratin sponge scaffolds for long-term cell cultivation." Journal of Biotechnology, vol. 93, 2002 pp. 165-170.

Tanabe, T.; Tachibana, A.; Yamauchi, K.; "Keratins: prospective proteinous biomaterial."; Recent Research Developments in Protein Engineering; vol. 1(Pt.2),2001, pp. 247-259.

Tazawa, T.; et al; "Anti-hair keratin monoclonal antibody (HKN-2)."; The Journal of Dermatology; vol. 12, 1985, pp. 313-317.

Thomas, H.; et al; "Isolation of the microfibrillar proteins of wool in the disulfide form." Melliand Textilberichte; vol. 65, No. 3, 1984, pp. 208-209.

Tsai, A.G.; et al; "High viscocity plasma expanders: Volume restitution fluids for lowering the transfusion trigger."; Biorheology, vol. 38 (2-3), 2001, pp. 229-237.

Tsai, A.G.; et al; "The unusual properties of effective blood substitutes."; Keio Journal of Medicine; vol. 51 (1), 2002, pp. 17-20.

Tsuchida, E.; "Oxygen ligation of macromolecule-porphyrin complexes."; Journal of the Chemical Society of Japan; No. 6, 1988, pp. 845-852.

Tsuchida, E.; et al; "Cobalt (II)/poly(ethyleneimine) membrane with oxygen binding ability."; Makromolekulare Chemie; vol. 3 (10), 1982, pp. 693-696.

Tucker, D.J.; et al; "Variations in goat fiber proteins."; Australian Journal of Agriculture Research vol. 40, No. 3, 1989, pp. 675-683.

(56) References Cited

OTHER PUBLICATIONS

Ueyama, N.; et al; "A novel method for determining the chelation ability of the cysteine-containing peptides with 3,4-toluenedithiol. Application to .cents .2Fe-2S-ferredoxin model systems."; Bulletin of the Chemical Society of Japan; vol. 60 (1), 1987, pp. 283-287.
Van Neste, D.; "The growth of human hair in nude mice."; Dermatologic Clinics; vol. 14, No. 4, 1996, pp. 609-617.
Vasak, M.; et al; "Metal thiolate clusters in cobalt (II)-metallothionein."; Proceedings of the National Academy of Sciences of the United States of America; vol. 78 (11), 1981, pp. 6709-6713.
Vogeli, G.; et al; "High-Sulfur Protein Gene Expression in a Transgenic Mouse." Annals New York Academy of Sciences; vol. 642, 1991, pp. 21-30.
Ward, K.A.; et al.; "The structure of the wool keratin microfibrillar genes." Proceedings of the Australian Biochemical Society; vol. 15, 1983, pp. 70.
Ward, K.A.; "Changes in wool follicle keratinocyte protein-biosynthesis mediated by inhibitors of follicle bulb cell-proliferation."; Proceedings of the Australian Biochemical Society; vol. 9, 1976, vol. 9, pp. 57.
Ward, K.A.; "Study of keratin biosynthesis in isolated wool follicle cells." Proceedings of the Australian Biochemical Society; vol. 7, 1974, pp. 93.
Weber, K.; Geisler, N.; "The structural relation between intermediate filament proteins in living cells and the alpha-keratins of sheep wool" The EMBO Jjournal; vol. 1 No. 10, 1982, pp. 1155-1160.
Weiss, R.A.; Guilett, Y.A,G.; Freedberg, I.M.; Farmer, E.R.; Small, E.A.; Weiss, M.M.; Sun, T.T; "The use of monoclonal antibody to keratin in human epidermal disease: Alterations in immunohistochemical staining pattern." vol. 81, No. 3, 1983, pp. 224-230.
Werner, S.; et al.; "Large induction of keratinocyte growth factor expression in the dermis during wound healing." Proceedings of the National Academy of Sciences, USA; vol. 89, 1992, pp. 6896-6900.
Whitbread, L.A.; et al; "Expression of the intermediate filament gene, K15, in the basal cell layers of epithelia and the hair follicle."; Experimental Cell Research; vol. 244, 1998, pp. 448-459.
Widra, A.; "Ascoporogenesis by nannizzia grubyia on a soluble fraction of keratin." Mycopathologia et Mycologia Applicata; vol. 30, No. 2, 1966 pp. 141-144.
Wilson, B. W.; et al.; "Complete sequence of a type-I microfibrillar wool keratin gene."; Gene; vol. 73, No. 1, 1988, pp. 21-31.
Wilson, N.; et al; "The role of BMP-2 and BMP-4 in follicle initiation and the murine hair cycle."; Experimental Dermatology; vol. 8, No. 4, 1999, pp. 367-368.
Wolski, T.; Szumilo, H.; "Studies on the kinetics of dissolving feather keratin in the water-urea system." Acta Alimentaria Polinica; vol. 8, (32) No. 1-2, 1982, pp. 102-108.
Wormell, R. L.; "Regenerated fibers from wool." Brit. Rayon Silk Journal; vol. 26, No. 309, pp. 55, 1950.
Wormell, R.L.; "Regenerated protein fibres from wool and casein"; The Journal of the Textile Institute; vol. 39, 1948, T219-T224.
Wormell, R.L.; "Wool, silk and regenerated protein fibers—chemistry." Rev. Textile Progress; vol. 9, 1957, pp. 51-62.
Wortmann, F.J.; et al.; "A method for isolating the cortex of keratin fibers."; Textile Research Journal; vol. 52, 1982, pp. 479-481.
Yakubovich, T.N.; Teslenko, V.V.; Zub, Y.L; "Carriers of molecular oxygen on the basis of metal complexes incorporated in polyorganosiloxane matrices."; Journal of Inorganic and Organometallic Polymers; vol. 6, No. 1, 1996, pp. 43-49.
Yamamura, T.; et al; "Conformation control of peptides by metal ions. Coordination confirmation correlation observed in a model for Cys-X-Y-Cys/M2+ in proteins."; Inorganic Chemistry; vol. 36 (21), 1997, pp. 4849-4859.
Yamauchi, K. et al.; "Novel proteinous microcapsules from wool keratins." Colloids and Sudaces, B: Biointerfaces; vol. 9, 1997, pp. 117-119.
Yamauchi, K.; "Dissolution of hair and wool. Keratin polymers." Kobunshi Kako; vol. 4i, No. 1, 1994, pp. 14-19.

Yamauchi, K.; "Perspective in chemistry and applications of keratins." Kobunshi; vol. 50, No. 4, 2001, pp. 240-243.
Yamauchi, K.; "Polymer films fom keratin."; Fragrance Journal; vol. 21 (5), 1993, pp. 62-67.
Yamauchi, K.; "Preparation of stable aqueous solution of keratins, and physicochemical and biochemical properties of films." Polymer Preprints—American Chemical Society, Division of Polymer Chemistry; vol. 39, No. 1, 1998, pp. 357-358.
Yamauchi, K.; et al.; "Cultivation of Mouse L929 Fibroblast Cells on Keratins."; Kobunshi Gakkai Yokoshu (Polymer Preprints), Japan; vol. 44, No. 3,1995, pp. 503.
Yamauchi, K.; et al.; "Preparation of stable aqueous solution of keratins, and physicochemical and biodegradational properties of films." Journal of Biomedical Materials Research; vol. 31, No. 4, 1996, pp. 439-444.
Yamauchi, K.; et al; "Enhanced cell adhesion on RGDS-carrying keratin film."; Material Science & Engineering, C.: Biomimetic and Supermolecular Systems; vol. C23, No. 4, 2003, pp. 467-472.
Yao, X.; et al; "Oxygen carrying porphyrin-protein complexes the effect of iron (II) prophyrin structure on dioxygen binding performance."; Research Communications in Biochemistry and Cell & Molecular Biology; vol. 5 (1&2) 2001, pp. 171-174.
Yoshimizu, H.; et al; "C CP/MAS NMR study of the conformation of stretched or heated low-sulfur keratin protein films." Macromolecules,; vol. 24, 1991, pp. 862-866.
Zackroff, R.V.; Goldman, R.D.; "In vitro assembly of intermediate filaments from baby hamster kidney (BHK-21) cells." Proceedings of the National Academy of Sciences, USA; vol. 76, No. 12, pp. 6226-6230, 1979.
Zahn, H. et al.; "Reactivity of amino acid side chains. 18. Reactions of p-fluoro-m,m'-dinitrodiphenyl sulfone and p,p'-difluro-m,m'-dinitrodiphenyl sulfone with wool keratin and silk fibroin."; Kolloid Zeitschrift fuer Polymere; vol. 5, 1973 pp. 289-298.
Zahn, H. et al.; "Wool as a biological composite structure."; Industrial & Engineering Chemistry Product Research and Development; vol. 19, 1980, pp. 496-501.
Zahn, H.; "Progress report on hair keratin research."; International Journal of Cosmetic Science; vol. 24, 2002, pp. 163-169.
Zahn, H.; "Structure and chemistry of wool fibers." Kolloid-Z; vol. 100, 1942, pp. 283-298.
Zahn, H.; "The role of mohair keratin research." Melliand Textilberichte; vol. 72, 1991, pp. 926-931.
Zahn, H.; "Wool research taking part in comtemporary chemistry and physics." Arbeitsgemeinschaft Forsch. Landes Nordheim-Westfalen; vol. 75, 1957, pp. 47-80.
Zahn, H.G.; et al; "2-Dimensional keratin patterns of human hair including cosmetically treated ones."; Journal of Forensic Science Society; vol. 24, No. 4, 1984, pp. 432.
Zahn,H. et al.; "Wool as a biological compounding material." Schriftenreihe des Deutaschen Wollforschungsintitutes; vol. 76, 1978, pp. 18-25.
Crewther, W.G. et al; "Helix-rich fraction from the low-sulphur proteins of wool."; Nature; vol. 207,(4994), 1965, pp. 295.
Crewther, W.G.; Effect of aftertreatment on the stability of set wool fibers. Comments; Journal of the Society of Dyers and Colourist; vol. 86, No. 5, 1970, pp. 208.
Crewther, W.G.; "The concept of internal pH in wool fibers and the interpretation of data relating to setting."; Journal of the Society of Dyers and Colourist; vol. 81, (4), 1965, pp. 156-158.
Crewther, W.G.; "The viscoelasticity of alpha keratin fibers."; Experimental Dermatology; vol. 8 (4), 1999, pp. 343-344.
Crewther, W.G.; "Preparation and properties of large peptides from the helical regiones of the low-sulfur proteins of wool."; Applied Polymer Symposia; vol. 18, No. 1, 1971, pp. 1-20.
Crewther, W.G.; "Structure of .alpha-keratin."; Textile Research Journal; vol. 42, No. 4, 1972, pp. 251-252.
Crewther, W.G.; "The stress-strain characteristics of animal fibers after reduction and alkylation."; Textile Research Journal; vol. 35, No. 10, 1965, pp. 867-877.
Crewther, W.G.; "Thiol-disulfide interchange reactions in the setting of single wool fibers." Journal of the Society of Dyers and Colourist; vol. 82, No. 1, 1966, pp. 54-58.

(56) References Cited

OTHER PUBLICATIONS

Crewther, W.G.; at al; "Effect of S-carboxymethylation of wool proteins on the iodination of tyrosine residues."; Textile Research Journal; vol. 41, No. 3, 1971, 99.267.
Crewther, W.G.; Dowling, L.M.; "The relation between the disulphide content of wool and the two-stage supercontraction of wool fibers in solution of LiBr."; Biochimica et Biophysica Acta; vol. 46, 1961, pp. 605-606.
Crewther, W.G.; et al; "Amino acid sequences of alpha-helical segments from S-carboxymethylkerateine-A. Complete sequence of a type II segment."; Biochemical Journal; vol. 173 (2), 1978, pp. 365-371.
Crewther, W.G.; et al; "Amino acid sequences of α-helical segments from S-carboxymethlykerateine-A. Tryptic and chymotryptic peptides from a type—II segment."; Biochemistry Journal; vol. 173, 1978 pp. 353-363.
Crewther, W.G.; et al; "Formation of various crosslinkages in wool and their effect on the supercontraction properties of the fibers."; Textile Research Journal; vol. 37, No. 9, 1967, pp. 736-745.
Crewther, W.G.; et al; "Low-sulfur proteins from α-keratins. Inter-relationship between their amino acid compositions, α-helix contents, and the supercontraction of the parent keratin." Biopolymers, vol. 4, 1966, pp. 905-916.
Crewther, W.G.; et al; "Reduction of S-carboxymethlycysteine and methionine with sodium in liquid ammonia." Biochimica et Biophysica Acta; vol. 164, 1969, pp. 606-609.
Crewther, W.G.; et al; "Structure of intermediate filaments."; International Journal of Biological Macrmolecules; vol. 5, No. 5, 1983, pp. 267-274.
Crewther, W.G.; et al; "The chemistry of keratins."; Advance Protein Chemistry; vol. 20, 1965 pp. 191-346.
Crewther, W.G.; et al; "The preparation and properties of a helix-rich fraction obtained by partial proteolysis of low sulfur S-Carboxymethylkerateine from wool." The Journal of Biological Chemistry; vol. 242, No. 19, 1967, pp. 4310-4319.
Dale, H.N.; "Keratin and other coatings for pills."; Pharmacology Journal; vol. 129, 1932, pp. 494-495.
Damaglou, A.P.; et al; "The hydrolysis by thermolysin of dipeptide derivatives that contain substituted cysteine" Biochemical Journal; vol. 123, No. 3, 1971, pp. 379-384.
Darskus, R.L.; et al.; "Breed and species differences in the hair proteins of four genera of caprini." Australian Journal of Biological Sciences; vol. 24, 1971, pp. 515-524.
Darskus, R.L.; et al; "The possibility of common amino acid sequences in high sulphur protein fractions from wool." Australian Journal of Biological Sciences; vol. 22, 1969, pp. 1197-1204.
De Sanctis, G.; et al; "Mini-myoglobin—Electron paramagnetic resonance and reversible oxygenation of the cobalt derivative."; Journal of Molecular Biology; vol. 222, 1991, pp. 637-643.
Dedeurwaerder, R.A.; et al; "Selective extraction of protein fraction from wool keratin." Nature vol. 203, 1964, pp. 48,49.
Dobb, M.G.; et al; "Electron microscopy of fibrous keratins."; Symposuim of fibrous protein, Int Conf.; 1967, pp. 267-278.
Dowling, L.M.; Crewther, W.G.; Inglis, A.S.; "The primary structure of component 8c-1, a subunit protein of intermediate filaments in wool keratin."; Biochemistry Journal vol. 236, 1986, pp. 695-703.
Dowling, L.M.; Crewther, W.G.; Parry, D.A.D.; "The secondary structure of component 8c-1, of alpha-keratin."; Biochemistry Journal; vol. 236, 1986, pp. 705-712.
Dowling, L.M.; et al; "Effect of the solvent on the iodanation of a tyrosine derivative and its relation to iodination of wool."; Textile Research Journal; vol. 41, No. 1, 1971, pp. 65-69.
Dowling, L.M.; et al; "Isolation of components from the low sulphur proteins of wool by fractional precipitation."; Preparative Biochemistry, vol. 4(3), 1974, pp. 203-226.
Downes, A.M.; et al; "Evaluation of modified [35S] methionine and [35S] casein preparations as supplements for sheep"; British Journal of Nutrition; vol. 24, No. 4, 1970, pp. 1083-1089.
Downes, A.M.; et al; "Matabolic fate of parenterally administered sulphur containing amino acids in sheep and the effects on growth and composition of wool"; Australian Journal of Biological Sciences; vol. 23, No. 5, 1970, pp. 1077-1088.
Downes, A.M.; Ferguson,K.A.; Gillespie, J.M.; Harrap, B.S.; "A study of the proteins of the wool follicle." Australian Journal of Biological Science; vol. 19. 1966, pp. 319-333.
Dunn, S.M.; et al; "Regulation of hair gene expression."; Experimental Dermatology, vol. 8, 1999, pp. 341-342.
Earland, C.; et al; "Structure of keratin. II. Amino acid content of fractions isolated from oxidized wool."; Biochimica et Biophysica Acta; vol. 22, 1956, pp. 405-411.
Ebright, Y.W.; et al; "N-(lodoacetyl)-p-phenylenediamine—EDTA: A regent for high-efficiency incorporation of an EDTA-metal complex at a rationally selected site within a protein."; Bioconjugate Chemistry; vol. 4 (3), 1993, pp. 219-225.
Edwards, B.; et al; "Chemical studies on powdered keratins." Journal of Biological Chemistry; vol. 154, 1944, pp. 593-596.
Elleman, T.C.; et al; Amino acid sequences of alpha-helical segments from S-carboxymethylkerateine-A. Statistical analysis; Biochemical Journal; vol. 173 (2), 1978, pp. 387-391.
Elleman, T.C.; et al; "Periodicity in high sulphur proteins from wool"; Nature; vol. 246, 1973, pp. 530-531.
Elod, E.: et al.; "Reactions of wool fiber and alterations in the fine structure,"; Melliand Textillber; vol. 21, 1940, pp. 385-388.
Elod, E.; et al.; The nature of the reactivity of wool, Melliand Textilber; vol. 21, 1940, pp. 617-622.
Elod, E; et al; "The structure and reactivity of the woolen fiber. IX. The effect of H2O2 on wool."; Melliand Textilber; vol. 23, 1942, pp. 313-316.
Elod,E. et al.; "The infiltration of heavy metal sulfides in the keratin fiber." Chem Ber. vol. 74B, 1941, pp. 1759-1762.
Eriksson, A.; et al.; "PDGF—α- and β-receptors activate unique and common signal transduction pathaways."; The EMBO Journal; vol. 11, 1992, pp. 543-550.
Filshie, B.K. et al; "The Fine Structure of α-Keratin." Journal of Molecular Biology; vol. 3, 1961, pp. 784-786.
Filshie, B.K.; Rodgers, G.E.; "An electron microscope study of the fine structure of feather keratin."; The Journal of Cell Biology; vol. 13, 1962, pp. 1-12.
Frank, S.; et al.; "Transforming growth factors β1,β2, and β3 and their receptors are differentially regulated during normal and impaired wound healing." The Journal of Biological Chemistry; vol. 271, 1996, pp. 10188-10193.
Frankel, M.J.; Powell, B.C.; Ward, K.A.; Sleigh, M.J., Rodgers, G.E.; "The keratin BIIIB gene family: Isolation of cDNA clones and stucture of a gene and a related pseudogene."; Genomics vol. 4, 1989, pp. 182-191.
Fraser, B.R.D, et al; "Intermediate Filaments in α-keratins." Proceeedings of the National Academy of Sciences, USA.; Biochemistry; vol. 83, 1986, pp. 1179-1183.
Fraser, R.D.B.; et al; "Disulphide bonding in α-keratin."; International Journal of Biological Macromolecules; vol. 10, issue 2, 1988, pp. 106-112.
Fraser, R.D.B.; et al; "Microscopic Observations of the Alkaline-Thioglycollate Extraction of Wool." Short Communications, Wool Textile Research Laboratory; vol. 12, 1953, pp. 484-485.
Fraser, R.D.B.; et al; "Molecular organization in Alpha-Keratin."; Nature; vol. 193, 1962, pp. 1052-1055.
Fraser, R.D.B.; Gillispie, J.M.; "Wool structure and biosysnthesis." Nature vol. 126 1976, ppp. 650-654.
Fraser, R.D.B.; Macrae, T.P.; "Helical models of feather keratin structure." Nature; vol. 195, No. 4847, 1962, pp. 1167,1168.
Fraser, R.D.B.; MaCrae, T.P.; Rogers, G.E.; "Structure of Alpha-Keratin." Nature; vol. 183, 1959, pp. 592-594.
Fraser,R.D.B.; Gillespie, J.M.; Macrae,T.P.; "Tyrosine-rich proteins in keratins."; Comparative Biochemistry and Physiology; vol. 44B, 1973, pp. 943-949.
Fratini, A.; et al; "Dietary cysteine regulates the levels of mRNAs encoding a family of cysteine-rich proteins of wool."; Journal of Investigative Dermatology; vol. 102, 1994, pp. 178-185.
Frenkel, M.J. et al.; "Heterogeneity of tyrosine-rich proteins of wool."; Proceedings of the Australian Biochemical Society; vol. 7, 1974, p. 4.

(56) References Cited

OTHER PUBLICATIONS

Frenkel, M.J.; "Alkali susceptible amides in tyrosine-rich proteins of wool."; Proceedings of the Australian Biochemical Society; vol. 10, 1977, p. 21.
Frenkel, M.J.; et al.; "Studies of the ribonucleic-acids coding for the keratin complex of hair."; Proceedings of the Australian Biochemical Society; vol. 12, 1979, pp. 87.
Frenkel, M.J.; et al; "Factors influencing biosynthesis of tyrosine-rich proteins of wool."; Australian Journal of Biological Sciences; vol. 27, 1974, pp. 31-38.
Frenkel, M.J.; et al; "The keratin BIIIB gene family: isolation of cDNA clones and structure of a gene and a related pseudogene."; Genomics; vol. 4, No. 2, 1989, pp. 182-191.
Frenkel, M.J.; Gillespie, J.M.; Reis, P.J.; "Studies on the inhibition of synthesis of the tyrosine-rich proteins of wool."; Australian Journal of Biological Sciences; vol. 28, 1975, pp. 331-338.
Frenkel, M.J.; Gillespie, J.M.; Woods, E.F.;"The isolation and properties of a tyrosine-rich protein from wool: component 0.62."; European Journal Biochemistry; vol. 34, 1973, pp. 112-119.
Fujisawa, K.; et al; "Synthesis and characterization of zinc family thiolato complexes.";Abstracts, Symposium on Biofunctional Chemistry, vol. 14, 1999, pp. 52-53.
Gillespie, J.M. et al; "Evidence of homology in a high-sulphur protein fraction (SCMK-B2) of wool and hair $\alpha$-keratins."; Biochemistry Journal; vol. 110, No. 2, 1968, pp. 193-198.
Gillespie, J.M. et al; "A comparative study of high-sulphur proteins from $\alpha$-karatins." Comparative Biochemistry and Physiology; vol. 15, 1965, pp. 175-185.
Gillespie, J.M.; "Reaction of Sodium Borohydride with wool." Nature; vol. 183 No. 4657, 1959, pp. 322, 323.
Gillespie, J.M.; "Swelling of keratins in formic acid." Textile Research Journal; vol. 40, No. 9, 1970, pp. 853-855.
Gillespie, J.M.; "The isolation and properties of some soluble proteins from wool. (II) The preferential extracation of high-sulphur proteins."; Australian Journal of Biological Sciences; vol. 15, No. 1, 1962, pp. 262-277.
Gillespie, J.M.; "The isolation from wool of a readily extractable protein of low sulphur content." Biochimica et Biophysica Acta; vol. 27, 1958, pp. 225,226.
Gillespie, J.M.; "The probable role and location of high-glycine-tyrosine proteins in the structure of keratins." Biopolymers, vol. 17, 1978, pp. 2743-2745.
Gillespie, J.M.; "The relation between the crimp of wool and its content of high-sulfur proteins."; Textile Research Journal; vol. 35, No. 12, 1965, pp. 1128-1129.
Gillespie, J.M.; "Keratin structure and changes with copper deficiency."; *Australian Journal of Dermatology*; vol. 14, No. 3, 1973, pp. 127-131.
Gillespie, J.M.; Broad, A.; "A further study on the dietary-regulated biosynthesis of high-sulphur wool proteins." Biochemistry Journal; vol. 112, 1969, pp. 41-49.
Gillespie, J.M.; Darskus, R.L.; "Relation between the tyrosine content of various wools and their content of a class of protiens rich in tyrosine and glycine."; Australian Journal Biological Science; vol. 24, 1971, pp. 1189-1197.
Gillespie, J.M.; et al.; "Changes in the matrix proteins of wool and mouse hair following the administration of depilatory compounds." Australian Journal of Biological Sciences; vol. 33, 1980, pp. 125-136.
Gillespie, J.M.; et al.; "Proteins of the hard keratins of Echidna, Hedgehog, Rabbit, Ox and Man."; Australian Journal of Biological Sciences, vol. 30, 1977, pp. 401-409.
Gillespie, J.M.; et al; "The Diversity of Keratins"; Comparative Biochemistry and Physiology; vol. 47, No. 2,1974, pp. 339-346.
Gillespie, J.M.; et al; "Variable composition of hair and high-sulfur proteins in trichothiodystrophy."; Journal of Applied Cosmetology; vol. 7, No. 2, 1989, pp. 39-48.
Gillespie, J.M.; Frenkel, M.J.; "The macroheterogeneity of type I tyrosine-rich proteins of merino wool."; Australian Journal Biological Science; vol. 27, 1974, pp. 617-627.

Gillespie, J.M.; Inglis, A.S.; "High-sulphur proteins as a major cause of variation in sulphur content between $\alpha$-keratins." Nature; vol. 207, 1965, pp. 1293,1294.
Gillespie, J.M.; Marshall, R.C.; "A comparision of the proteins of normal and trichothiodystrophic human hair." The Journal of Investigative Dermatology; vol. 80, 1983, pp. 195-202.
Gillespie, J.M.; Marshall, R.C.; Moore, G.P.; Panaretto, B.A.; Robertson, D.M.; "Changes in the proteins of wool following treatment of sheep with epidermal growth factor."; The Journal of Investigative Dermatology; vol. 79, No. 3, 1982, pp. 197-200.
Gillespie, J.M.; Reis, P.J.; "The dietary regulated biosynthesis of high-sulphur wool proteins."; Biochemistry Journal; vol. 98, 1966, pp. 669-677.
Gillespie, J.M.; Simmonds, D.H.; "Amino acid composition of a sulphur-rich protein from wool."; Biochimica et Biophysica Acta; vol. 39, 1960, pp. 538-539.
Gillespie,J.M.; "Proteins rich in glycine and tyrosine from keratins."; Comparative Biochemistry and Physiology; vol. 41B, 1972, pp. 723-734.
Alexander, P.; Earland, C.; "Structure of wool fibers—Isolation of an $\alpha$ and $\beta$-protein in wool." Nature; vol. 166, 1950.
Almog, J.; et al; "Reversible binding of dioxygen to mesoporphyrin IX derivatives at low temperatures."; Journal of the American Chemical Society; vol. 96(17), 1974, pp. 5600-5601.
Almog, J.; et al; "Reversible oxygenation and autoxidation of a capped porphyrin iron (II) complex."; Journal of the American Chemical Society; vol. 97(1), 1975, pp. 227-228.
Amiya, T.; et al; "Conformational studies of the $\alpha$-helical proteins from wool keratins by c.d." International Journal of Biological Macromolecules; vol. 4, 1982, pp. 165-172.
Ando, H.; et al; "Separation and characterization of keratin components of merino wool. III: Removal of cuticle by ultrasonic irradiation." Bulletin of the Institute for Chemical Research, Kyoto University; vol. 31, No. 3, 1975, pp. 81-85.
Ashkenasy, G.; et al; "Assemblies of "hinged" iron-porphyrins as potential oxygen sensors."; Journal of the American Chemical Society; vol. 122, No. 6, 2000, pp. 1116-1122.
Baldwin, J.E.; et al; "Binding of dioxygen to iron (II), Reversible behavior in solution."; Journal of the American Chemical Society; vol. 95 (17), 1973, pp. 5757-5759.
Barr, M.; "Oxidation, reduction and hydroysis of wool keratin."; Iowa State Coll. Journal of Science, vol. 12, 1937, pp. 106-107.
Bawden, C.S.; et al; "Expression of bacterial cysteine biosynthesis genes in transgenic mice and sheep: toward a new in vivo acid biosynthesis pathway and improved wool growth." Transgenic Research; vol. 4,1995, pp. 87-104.
Bawden, C.S.; et al; "Expression of wool intermediate filament keratin transgene in sheep fibre alters structure."; Transgenic Research; vol. 7, 1998, pp. 273-287.
Bawden, C.S.; et al; "Improvement of wool quality by transgenesis."; Science Update, Conf: OECD, 2001, pp. 67-76.
Bawden, C.S.; et al; "Sheep transgenesis with keratin and non-keratin genes: expression in the wool follicle for the modified fibre properties and growth rates."; Experimental Dermatology; vol. 8, 1999, pp. 342-343.
Berse, B.; et al.; "Vascular permeability factor (Vascular endothelial growth factor) gene is expressed differentially in normal tissues, macrophages, and tumors." Molecular Biology of the Cell; vol. 3, 1992, pp. 211-220.
Besse, D.; et al; "Synthesis of selenocysteine peptides and their oxidation to diselenide-bridged compounds."; Journal of Peptide Science; vol. 3 (6), 1997, pp. 442-453.
Bettex-Galland, M. et al.; "Advances in Protein Chemistry." Academic Press, vol. 20, 1965.
Bhatnagar, G.M. et al; "Difference spectra of kerateine-B."; *International Journal of Protein Research*; vol. 1 No. 3, 1969, pp. 213-219.
Bhatnagar, G.M.; et al; "Assessment of confirmational changes in low-sulfur S-(carboxymethyl)keratin from wool."; Australian Journal of Biological Sciences; vol. 20, No. 4, 1967, pp. 827-836.

(56) References Cited

OTHER PUBLICATIONS

Bhatnagar, G.M.; et al; "The conformation of the high sulphur proteins of wool. I The preparation and properties of a water soluble metakeratin."; International Journal of Protein Research; vol. 1 (3), 1969, pp. 199-212.

Bhatnagar, G.M.; et al; "The conformation of the high-sulphur proteins of wool. II—Difference spectra of kerateine-B." International Journal of Protein Research I; 1969, pp. 213-219.

Blagrove, R.J.; Frenkel, M.J.; Gillespie, J.M.; "The electrophoresis of the high-tyrosine proteins of keratins on cellulose acetate strips."; Comparative Biochemistry Physiologoly; vol. 50B, 1975, pp. 571-572.

Blessing, M.; et al.; "Transgenic mice as a model to study the role of TGF-β-related molecules in hair follicles." Genes and Development; vol. 7, 1993, pp. 204-215.

Bradbury, J.H.; "The structure and chemistry of keratin fibers." Advanced Protein Chemistry; vol. 27, 1973, pp. 111-211.

Bradbury, J.H.; et al.; "Advances in Protein Chemistry." vol. 27, 1973, pp. 222-375.

Bradbury, J.H.; et al; "Observations by light and electron microscopy on wool cuticle fractions obtained by ultrasonics."; Textile Research Journal; vol. 33, No. 4, 1963, pp. 251-257.

Bradbury, J.H.; et al; "Separation of chemically unmodified histiological components of keratin fibers and analyses of cuticles."; Nature; vol. 210, No. 5043, 1966, pp. 1333-1334.

Breinl, F.; et al; "The oxidative breaking up of keratin through treatment with hydrogen peroxide." Z.Physiol. Chemistry; vol. 52, 1907, pp. 158-169.

Broad, A.; Gillespie, J.M., Reis, P.J.; "The influence of sulphur-containing amino acids on the biosynthesis of high-sulphur wool proteins." Australian Journal of Biological Sciences; vol. 23, 1970, pp. 149-164.

Brown, L.F.; et al.; "Expression of vascular permeability factor (Vascular Endothelial Growth Factor) by epidermal keratinocytes during wound healing."; Journal of Experimental Medicine; vol. 176, 1992, pp. 1375-1379.

Brunner, H.; Brunner, A.; "Fractionation of tyrosine-rich proteins from oxidized wool by ion-exchange chromotography and preparative electrophoresis."; European Journal Biochemistry; vol. 32, 1973, pp. 350-355.

Bryson, W.G.; et al; "The analytical tools of proteomics provide new insights into the expression of the wool genome, keratin chemistry and textile processing."; Wool Tcehnology and Sheep Breeding; vol. 49, No. 4, 2001, pp. 246-260.

Cameron, J.H.; et al; "Nickel (II) and cobalt (II) complexes of potentially quinquedentate macrobicyclic ligands. Reversible binding to dioxygen to a cobalt (II) complex."; Journal of the Chemical Society, Dalton Transactions: Inorganic Chemistry; vol. 3, 1993, pp. 397-402.

Campbell, M.E.; Whiteley, K.J.; Gillespie, J.M.; "Compositional studies of high and low-crimp wools."; Australian Journal of Biological Sciences; vol. 25, 1972, pp. 977-987.

Carey, J.R.; et al; "Design and synthesis of novel metalloproteins through reversible encapsulation of metal complexes by proteins." Abstract of Papers, 222nd ACS National Meeting, 2001.

Chatani, E.; et al; "A film formation technology of wool keratin."; Textile and Fashion; vol. 14(5), 1997, pp. 227-235.

Chatani, E.; et al; "Research on merchandizing technology of wool keratin. Film formation technology of wool keratin."; Owari Textile Research Annual Report No. 93, 1998, pp. 93-101.

Clark, R.A.F. Editor; "The Molecular and Cellular Biology of Wound Repair."; Plenum Press 2nd Edition, 1996, 1988.

Japanese Office Action Corresponding to Japanese Patent Application No. 2008-555408; Dispatch Date: Apr. 24, 2012; 3 pages (Foreign Text Only).

Alvis, MR, et al., NeuColl, Inc., Palo Alto, CA, Successful Induction of New Bone Formation by Collagraft (Mar. 12-15, 2000) 46th Annual Meeting of the Orthopaedic Research Society, Orlando, FL.

Cornell, CN, Long-Term Results Associated with the Use of Collagen-Calcium Phosphate (Collagraft®) as a Bone Graft Substitute in Fractures and Non-Unions of the Humeral Shaft (Oct. 18-20, 2001) Orthopaedic Trauma Association Annual Meeting, San Diego, CA.

Crewther WG et al., The Chemistry of Keratins. Anfinsen CB Jr et al., editors. Advances in Protein Chemistry (1965) Academic Press. New York:191-346.

Goddard et al., A Study on Keratin. J. Biol. Chem. 106:605-14 (1934).

International Search Report and Written Opinion Corresponding to International Application No. PCT/US06/40673; Sep. 24, 2007.

Lee SJ et al. Tissue Engineering Scaffolds From Self-assembled Human Hair Keratins (2005) Polymer Preprints 46(1):112.

Migneault et al. Glutaraldehyde: behavior in aqueous solution, reaction with proteins, and application to enzyme crossing. BioTechniques, 2004; 37(5): 790-802.

Mitsui S, Ohuchi A, Hotta M, Tsuboi R, Ogawa H. Genes for a range or growth factors and cyclin-dependent kinase inhibitors are expressed by isolated human hair follicles. *British J Dermatol.* 1997;137: 693-698.

Muzzarelli et al. "Chitosan-oxychitin coating for prosthetic materials", *Carbohydrate Polymers*, 2001, 45:35-41.

NeuColl, Inc., Clinical Performance of Collagraft® Bone Graft Matrix in the Management of Fractures and Osseous Defects in the Appendicular Skeleton (Jan. 2000).

O'Donnell IJ et al. Studies on Oxidized Wool IV. Fractionation of Proteins Extracted from Wool on DEAE-cellulose Using Buffers Containing 8M Urea (1961) Aust J Biol Sci 14:461-474.

Supplementary European Search Report and Opinion, EP 07750473, mailed Feb. 2, 2010.

Tachibana A et al. Rapid fabrication of keratin-hydroxyapatite hybrid sponges toward osteoblast cultivation and differentiation. *Biomaterials.* 2005; 26: 297-302.

Thomas H et al. In vitro reconstitution of wool intermediate filaments. Int. *J. Biol. Macromol.* Oct. 1986; 8: 258-264.

Thompson et al., Studies on Reduced Wool. *Aust. J. Biol. Sci.* 15:757-68 (1962).

Yamauchi, The development of Keratin: Characteristics of Polymer Films. Fragrance J. 21(5):62-67 (1993). (English Translation of Entire Document).

New Zealand Examination Report Corresponding to New Zealand Patent Application No. 610387; Dated: Oct. 11, 2013; 2 Pages.

Hill P et al. Some properties of keratin biomaterials: Kerateines. Biomaterials. Feb. 1, 2010; 31(4): 585-693.

Supplementary Search Report and Search Opinion, EP 11841674.2, mailed May 19, 2014.

International Search Report and Written Opinion, PCT/US11/61190, mailed Feb. 14, 2013.

Marshall, R.C.; et al; "High sulphur proteins and α-keratins II. Isolatioin and partial characterization of purified components from mouse hair."; Australian Journal of Biological Sciences.; vol. 29, 1976, pp. 11-20.

Marshall, R.C.; et al; "High sulphur proteins from α-keratins I. Heterogeneity of the proteins from mouse hair."; Australian Journal of Biological Sciences; vol. 29, 1976, pp. 1-10.

Marshall, R.C.; et al; "Possible identification of specialty fibers y electrophoresis."; Textile Research Journal; vol. 54, No. 2, 1984, pp. 126-128.

Marshall, R.C.; et al; "Protein changes after short thermal treatments of wool fibrics."; Textile Research Journal; vol. 53, No. 12, 1983, pp. 792-794.

Marshall, R.C.; et al; "Sequence studies of wool proteins rich in glycine and aromatic residues."; Proceedings of the Australian Biochemical Society; vol. 12, 1979, pp. 12.

Marshall, R.C.; Gillespie, J.M.; "The keratin proteins of wool, horn and hoof from sheep." Australian Journal of Biological Sciences; vol. 30, 1977, pp. 389-400.

Marshall, R.C; et al.; "Heterogeneity and incomplete disulfide reduction in the high sulphur proteins of wool." Australian Journal of Biological Sciences; vol. 31, 1978, pp. 219-229.

Martin, P. "Wound Healing-Aiming for Perfect Skin Regeneration."; Science; vol. 276, 1997, pp. 75-81.

Mason, E.D.; et al.; "Dorsal midline fate in *Drosophila* embryos requires twisted gastrulation, a gene encoding a secreted protein

(56) References Cited

OTHER PUBLICATIONS related to human connective tissue growth factor." Genes and Development vol. 8, 1994, pp. 1489-1501.

Matsunaga, A.; et al; "Studies on the chemical property of human hair keratin. Part I. Fractionation and amino acid composition of human hair keratin solubilized by performic acid oxidation."; Hikaku Kagaku; vol. 27(1), 1981, pp. 21-29.

Mazzoni, M.C.; et al; "Blood and plasma viscocity and microvascular function in hemodilution. A perspective from LaJolla, California."; European Surgical Research; vol. 34, (1-2), 2002 Ref. 35.

McCloghry, C.E.; et al; "Wool follicles initiate, develop and produce fibres in ovine foetal skin grafts."; Proceedings of the Australian Society of Animal Production; vol. 18, 1990, pp. 518.

McMillin, D.R.; Holwerda, R.A.; Gray, H.B.; "Preparation and spectroscopic studies of cobalt (II) stellacyanin"; Proceedings of the National Academy of Sciences; vol. 71, No. 4, 1974, pp. 1339-1341.

McMillin, D.R.; Rosenberg, R.C.; Gray, H.B.; "Preparation and spectroscopic studies of cobalt (II) derivatives of blue copper proteins."; Proceedings of the National Academy of Sciences; vol. 71, No. 12, 1974, pp. 4760-4762.

Mies, H.H.; et al.; "Preparation of soluble proteins from wool."; Leder; vol. 39, 1988, pp. 1-9.

Mies, H.H.; Zahn, H.; "Chromatographic and electrophoretic investigations of the properties of unprotected low-sulphur wool keratins."; Journal of Chromatography; vol. 405, 1987, pp. 365-370.

Mitsui, S.; Ohuchi, A; Hotta, M.; Tsuboi, R.; Ogawa, H.; "Genes for a range of growth factors and cyclin-dependent kinase inhibitors are expressed by isolated human hair follicles." British Journal of Dermatology; vol. 137, 1997, pp. 693-698.

Miwa, M.; et al; "Effects of fiber length on the tensile strength of epoxy/glass fiber and polyester/glass fiber composites." Journal of Applied Polymer Science; vol. 25, 1980, pp. 795-807.

Miyamoto, T.: et al; "Sorption Behavior of Heavy Metal Ions on S-Subtituted Kerateine Gels." Institute for Chemical Research; vol. 34, No. 10, 1978, pp. T-447-T-454.

Moll, R.; et al.; "The catalog of humans cytokeratins: Patterns of expression in normal epithelia, tumors and cultured cells." Cell; vol. 31, 1982, pp. 11-24.

Mueller, R.V.; et al.; "The effect of insulinlike growth factor I on wound healing variables and macrophages in rats." Archives of Surgery; vol. 129, 1994, pp. 262-265.

Nakamura, A.; et al; "Cysteine-containing oligopepetide model complexes of iron-sulfur proteins."; Advances in Inorganic Chemistry; vol. 33, 1989, pp. 39-67.

Nakamura, Y.; et al; "Cystine in wool. Relation between sulfhydryl group and supercontraction." Sen-i Gakkaishi, vol. 16, 1960, pp. 852-858.

Nancarrow, M.J. et al; "Expression of ornithine decarboxylase during embryonic development of wool follicles."; Experimental Dermatology; vol. 8, 1999, pp. 362-368.

Noishiki, Y.; et al; "Application of denatured wool keratin derivatives to an antithrombogenic biomaterial. Vascular graft coated with a heparinized keratin derivative."; Kobunshi Ronbunshu; vol. 39(4), 1982, pp. 221-227.

Norman, J.A.T.; et al; "Reversible complexes for the recovery of dioxygen."; Procedings of the Annual IUCCP Symposium; 1987, pp. 107-125.

Okamoto, S.; "Formation of films from some proteins."; Nippon Shokuhin Kogyo Gakkaishi; vol. 24(1), 1977, pp. 40-50.

O'Shea, J.M.; et al; "The effect of ultrasonic irradiation on proteins." Australian Journal of Biological Sciences; vol. 26, 1973, pp. 583-590.

Osterberg, R.; "Metal complexes of peptides."; Metal Catalog Lipid Oxidation; Sv. Inst. Konserveringsforsk, Symposium, Goteberg Sweden, 1967, pp. 119-127.

Panteleyev, A.A.; et al.; "Hair follicle predetermination."; Journal of Cell Science; vol. 114, 2001, pp. 3419-3431.

Parry, D.A.D.; et al; "Fibrous proteins: Scientific, Industrial and Medical aspects."; An Academic Press Fast Publication; vol. 1, 1979, pp. 1-132.

Parry, D.A.D.; et al; "Structure of α-keratin: Structural implication of the amino acid sequences of the type I and type II chain segments."; Journal of Molecular Biology; vol. 113, 1977, pp. 449-454.

Pauling, L.; Corey, R.B.; "The structure of feather rachis keratin." Proceedings of the National Academy of Sciences; vol. 37, No. 5, 1951, pp. 256-261.

Pauling, L.; Corey, R.B.; "The structure of hair, muscle, and related proteins."; Proceedings of the National Academy of Sciences; vol. 37, No. 5, 1951, pp. 261-271.

Peters, L.; "Affinity of ions for keratin."; Journal of Textile Institute; vol. 58, No. 4, 1967, pp. 179-180.

Peus, D., et al.; "Growth factors in hair organ development and the hair growth cycle." Dermatologic Clinins; vol. 14, No. 4, 1996, pp. 559-572.

Philpott, M.P.; et al.; "Whole hair follicle culture." Dermatologic Clinics; vol. 14, No. 4, 1996, pp. 595-607.

Powell, B.C.; "The keratin proteins and genes of wool and hair."; Wool Technology and Sheep Breeding; vol. 44, No. 2, 1996, pp. 100-118.

Powell, B.C.; et al; "The Notch signalling pathway in hair growth."; Mechanisms of Development; vol. 78, 1988, pp. 189-192.

Powell, B.C.; et al; "Characterization of a gene encoding a cysteine-rich keratin associated protein synthesized late in rabbit hair follicle differentiation."; Differentiation; vol. 58, 1995, pp. 227-232.

Powell, B.C.; et al; "Characterization of hair (wool) keratin intermediate filament gene domain."; Journal of Investigative Dermatology; vol. 102, 1994, pp. 171-177.

Powell, B.C.; et al; "Mammalian keratin gene families: organization of genes coding for the B2 high sulphur proteins of sheep wool."; Nucleic Acids Research; vol. 11, 1983, pp. 5327-5346.

Powell, B.C.; et al; "Regulation of Keratin Gene Expression in Hair Follicle Differentiation." Annals New York Academy of Sciences; vol. 642, 1991, pp. 1-20.

Powell, B.C.; et al; "The role of keratin proteins and their genes in the growth, structure and properties of hair."; EXS; vol. 78, 1997, pp. 59-148 Ref: 284.

Powell, B.C.; et al; "Transgenic sheep and wool growth: possibilities and current status."; Reproduction, Fertility, and Development; vol. 6, 1994, pp. 615-623.

Powell, B.C.; Kemp, D.J.; Partington, G.A.; Gibbs, P.E.M.; Rogers, G.E.; "Control of feather keratin synthesis by the availability of keratin mRNA."; Biochemical and Biophysical research Communications; vol. 68, No. 4, 1976, pp. 1263-1271.

Powell, B.C.; Rodgers, G.E.; "Cyclic hair-loss and regrowth in the transgenic mice overexpressing and intermediate filament gene."; The EMBO Journal vol. 9, No. 5, 1990, pp. 1485-1493.

Rana, T.M.; et al; "Specific cleavage of a protein by an attached iron chelate."; Journal of the American Chemical Society; vol. 112 (6), 1990, pp. 2457-2458.

Randall, V.A.; "The use of dermal papilla cells in studies of normal and abnormal hair follicle biology."; Dermatologic Clinics; vol. 14, No. 4 1996 pp. 585-594.

Ranford, J.D.; et al; "Matallodrugs. The role of thiolate proteins and metal-thiolate complexes."; Metallothioneins, Conference General Review; 1992, pp. 408-435.

Ranshoff, S.; et al; "Synthesis and characterization of new dioxygen carriers: a reexamination of the fly-over ligand system."; Inorganic Chemistry; vol. 29(16), 1990, pp. 2945-2947.

Raphael, K.A.; et al; "Protein and amino acid composition of hair from mice carrying the naked (N) gene."; Genetic Research, vol. 44, No. 1, 1984, pp. 29-38.

Rappolee, D.A.; et al.; "Wound macrophages express TGF-α and other growth factors in vivo: Analysis by mRNA phenotyping."; Science; vol. 241, 1988, pp. 708-712.

Rau, H.K; Snigula, H.; Struck, A.; Robert, B.; Scheer, H.; Haehnel, W.; "Design, synthesis and properties of synthetic chlorophyll proteins."; European Journal of Biochemistry; vol. 268, 2001, pp. 3284-3295.

Reis, P.J.; "Influence of dietary protein and methionine on the sulphur content and growth rate of wool in the millk fed lambs" Australian Journal of Biological Science; vol. 23, No. 1, 1970, pp. 193-200.

(56) References Cited

OTHER PUBLICATIONS

Reis, P.J.; "The growth and composition of wool—III. Variations in the sulphur content of wool."; Australian Journal of Biological Sciences; vol. 18, 1965, pp. 671-687.
Reis, P.J.; "The growth and composition of wool. IV. The differential response of growth and of sulphur content of wool to the level of sulphur containing amino acids given per abomasum" Australian Journal of Biological Science; vol. 20, No. 4, 1967, pp. 809-825.
Reis, P.J.; et al; "The utilization of abomasal supplements of proteins and amino acids by sheep with special reference to wool growth"; Australian Journal of Biological Sciences; vol. 25, 1972, pp. 1057-1071.
Reis, P.J.; et al; "The influence of abomasal and intervenous supplements of sulphur containing amino acids on wool growth rate"; Australian Journal of Biological Sciences; vol. 26, No. 1, 1973, pp. 249-258.
Reis, P.J.; et al; "The nutritional control of the growth and properties of mohair and wool fibers: a comparative review"; Journal of Animal Science; vol. 72, No. 7, 1994, pp. 1899-1907.
Reis, P.J.; Gillespie, J.M.; "Effects of phhenylalanine and the analogues of methionine and phenylalanine on the composition of wool and mouse hair." Australian Journal of Biological Sciences; vol. 38, No. 2 pp. 151-163, 1985.
Reis, P.J.; Tunks, D.A.; Williams, O.B.; Williams, A. J.; "A relationship between sulphur content of wool and wool production by merino sheep."; Australian Journal of Biological Sciences; vol. 20, 1967, pp. 153-163.
Reis, P.J.; Variations in the S content of wool.; Biology Skin Hair Growth, Proceedings Symposium; 1964, pp. 365-375.
Rogers, G.E.; "Some observations on the proteins of the inner root sheath cells of hair follicles." Biochimica et Biophysica Acta; vol. 29. 1958, pp. 33-43.
Rogers, G.E. ; et al; "Keratin protofilaments and ribosomes from hair follicles."; Nature, vol. 205, 1965, pp. 77-78.
Rogers, G.E. et al.; "An approach to the investigation of protein biosynthesis in hair follicles." *Biology of Skin Hair Growth, Proceedings*, 1965, pp. 329-343.
Rogers, G.E.; "Genetic engineering for novel fibres."; Journal of the Textile Institute; vol. 91, part 3, Special Issue, 2000, pp. 24-31.
Rogers, G.E.; "Improvement of wool production through genetic engineering."; Trends in biotechnology (Personnal edition); vol. 8, 1990, pp. 6-11, 32 references.
Rogers, G.E.; "Proteins of the inner-root-sheath cells of hair follicles. "; Biochimica et Biophysica Acta; vol. 29, 1958, pp. 33-43.
Rogers, G.E.; "Structural and biochemical features of the hair follicles."; Epidermis; 1964, pp. 179-236.
Rogers, G.E.; "Structure and biochemistry of keratin."; The Biological Basis of Medicine.; vol. 6, 1969, pp. 21-57.
Rogers, G.E.; "Synthesis and cross-linking in the structure and growth of hair keratins." Clinics in Dermatology; vol. 6, No. 4, 1988, pp. 26-31.
Rogers, G.E.; et al; "Protein biosynthesis in hair follicles."; Biology of Skin Hair Growth., Proceedings ; 1965, pp. 329-343.
Rogers, G.E.; et al; "A procedure for the culture of hair follicles as functionally intact organoids."; Clinics in Dermatology; vol. 6, No. 4, 1988. pp. 36-41.
Rogers, G.E.; et al; "A sensitive assay for the enzyme activity in hair follicles and epidermis that catalyzes the peptidyl-arginine-citrulline posttranslational modification." Current Problems Dermatology; vol. 11, 1983, pp. 171-184.
Rogers, G.E.; et al; "Organization and expresson of hair follicle genes."; Journal of Investigative Dermatalogy; vol. 101, 1993, pp. 50 S-55 S.
Rogers, G.E.; et al; "Themes in the molecular structure of hair—discussion." Annals New York Academy Science; vol. 642, 1991, pp. 100-106.
Roop, D.R.; Cheng, C.K.; Titterington, L.; Meyers, C.A.; Stanley, J.R.; Steinert, P.M.; Yuspa, S.H.; "Synthetic peptides corresponding to keratin subunits elicit highly specific antobodies." The Journal of Biological Chemistry; vol. 259, No. 13 1984, pp. 8037-8040.
Ross, S.A.; et al; "Nickel complexes of cysteine- and cystine-containing peptides: Spontaneous formation of disulfide-bridged dimers at neutral pH."; Inorganic Chemistry, vol. 37 (20), 1998, pp. 5358-5363.
Rouse, J.G.; et al; "A review of keratin-based biomaterials for biomedical applications." Materials; vol. 3, 2010, pp. 999-1014.
Rowlands, R.J.; "Periodicity in high-sulphur proteins from wool."; Nature; vol. 246, No. 5434, 1973, pp. 530-531.
Sadova, S. F.; et al; "Grafting of vinyl monomers onto wool keratin in an oxidation-reduction system."; Zh. Vses. Khim. O-va, vol. 12(5), 1967, pp. 596-597.
Sander, G.; et al; "Expresssion of the homeobox gene, Barx2, in wool follicle development."; Journal of Investigative Dermatology; vol. 115, No. 4, 2000, pp. 753-756.
Sauk, J.J. et al; "Reconstitution of cytokeratin filaments in vitro: Further evidence for the role of nonhelical peptides in filament assembly."; The Journal of Cell Biology; vol. 99, 1984, pp. 1590-1597.
Schaller, J.; et al; "Membranes prepared from keratin-polyacrylonitrile graft copolymers." Journal of Applied Polymer Sciences; vol. 25(5), 1980, pp. 783-794.
Schornig, M.; Heumann, R.; Rohrer, H.; "Synthesis of nerve growth factor mRNA in cultures of developing mouse whisker pad, a peripheral target tissue of sensory trigeminal neurons."; The Journal of Cell Biology; vol. 120, No. 6, Mar. 1993, p. 1471-1479.
Schrooyen, P.M.M.; et al; "Biodegrable films from selectively modified feather keratin dispersions."; Polymer Preprints; vol. 39, No. 2, 1998, pp. 160.
Schrooyen, P.M.M.; et al; "Polymer films from chicken feather keratin."; Book of Abstracts, American Chemical Society National Meeting Boston, 1998.
Shah, M.; et al.; "Neutralisation of TGF-$\beta_1$ and TGF-$\beta_2$ or exogenous addition of TGF-$\beta_3$ to cutaneous rat wounds reduces scarring." Journal of Cell Science; vol. 108, 1995, pp. 985-1002.
Tachibana A et al. Modified keratin sponge: binding of bone morphogenetic protein-2 and osteoblast differentiation. Journal of Bioscience and Bioengineering. 2006; 102(5): 425-429.
U.S. Appl. No. 13/895,599, filed May 16, 2013, Van Dyke et al.

KERATIN COMPOSITIONS FOR TREATMENT OF BONE DEFICIENCY OR INJURY

RELATED APPLICATIONS

This application is a continuation under 35 U.S.C. 111(a) of PCT Application No. PCT/US2011/061190, filed Nov. 17, 2011, which in turn claims the benefit of U.S. Provisional Patent Application Ser. No. 61/414,748, filed Nov. 17, 2010, the disclosure of each of which is incorporated by reference herein in its entirety.

FIELD OF THE INVENTION

The present invention concerns keratin based graft compositions and methods of using the same.

BACKGROUND OF THE INVENTION

Regenerative medicine is a promising approach for the repair of bone deficiencies caused by trauma, degenerative diseases, and tumors. In the adult and elderly patient populations, however, significant changes in the multipotency of endogenous stem cells may hinder endogenous bone repair. Peroxisome proliferator-activated receptor gamma 2 (PPARγ2) has been shown to activate adipogenic and suppress osteogenic differentiation pathways in aged mice, limiting the potential effectiveness of regenerative treatments that involve endogenous and exogenous mesenchymal stem cells in bone tissue repair.

Alternative strategies useful for bone repair are therefore needed, particularly in the adult or elderly patient populations.

SUMMARY OF THE INVENTION

Provided herein are malleable bone graft compositions, including: (a) from 0 or 1 to 90 percent by weight keratose; (b) from 0 or 1 to 90 percent by weight kerateine; (c) from 0 to 3 percent or from 0 to 5 percent or from 0 to 10 percent or from 1 to 90 percent by weight particulate filler; (d) from 0 or from 0.001 to 5 percent by weight antibiotic; and (e) water or saline to balance. In some embodiments, the composition is or contains a hydrogel.

In some embodiments, the keratose is alpha/KAP keratose, gamma keratose, or mixtures thereof. In some embodiments, the kerateine is alpha/KAP kerateine, gamma kerateine, or mixtures thereof.

In some embodiments, the composition includes from 0, 5, or 10 to 90, 95 or 100 percent by weight keratose and/or from 90, 95 or 100 to 10, 5 of 0 percent by weight kerateine. In some embodiments, the composition includes from 0 to 30 percent by weight keratose and/or from 0 to 30 percent by weight kerateine. In some embodiments, the composition includes from 0.001 to 5 percent by weight bone morphogenic protein 2 (BMP2).

In some embodiments, the composition further includes stem cells (e.g., mesenchymal stem cells or adipose derived stem cells). In some embodiments, the cells human and from a donor who is at least 40, 45, 50, 55, 60, 65, 70 or 75 years old, or at least 60, 65, 70, 75 or 80 years old, at the time of harvest.

Also provided are methods of treating a fracture or a bone deficiency in a subject in need thereof, comprising administering a composition as provided herein to the subject in a treatment effective amount.

Further provided is the use of a composition as provided herein for the treatment of a fracture or bone deficiency, or the use of a keratin as provided herein in the preparation of a medicament for the treatment of a fracture or bone deficiency.

DETAILED DESCRIPTION OF THE PREFERRED EMBODIMENTS

Figure 1:
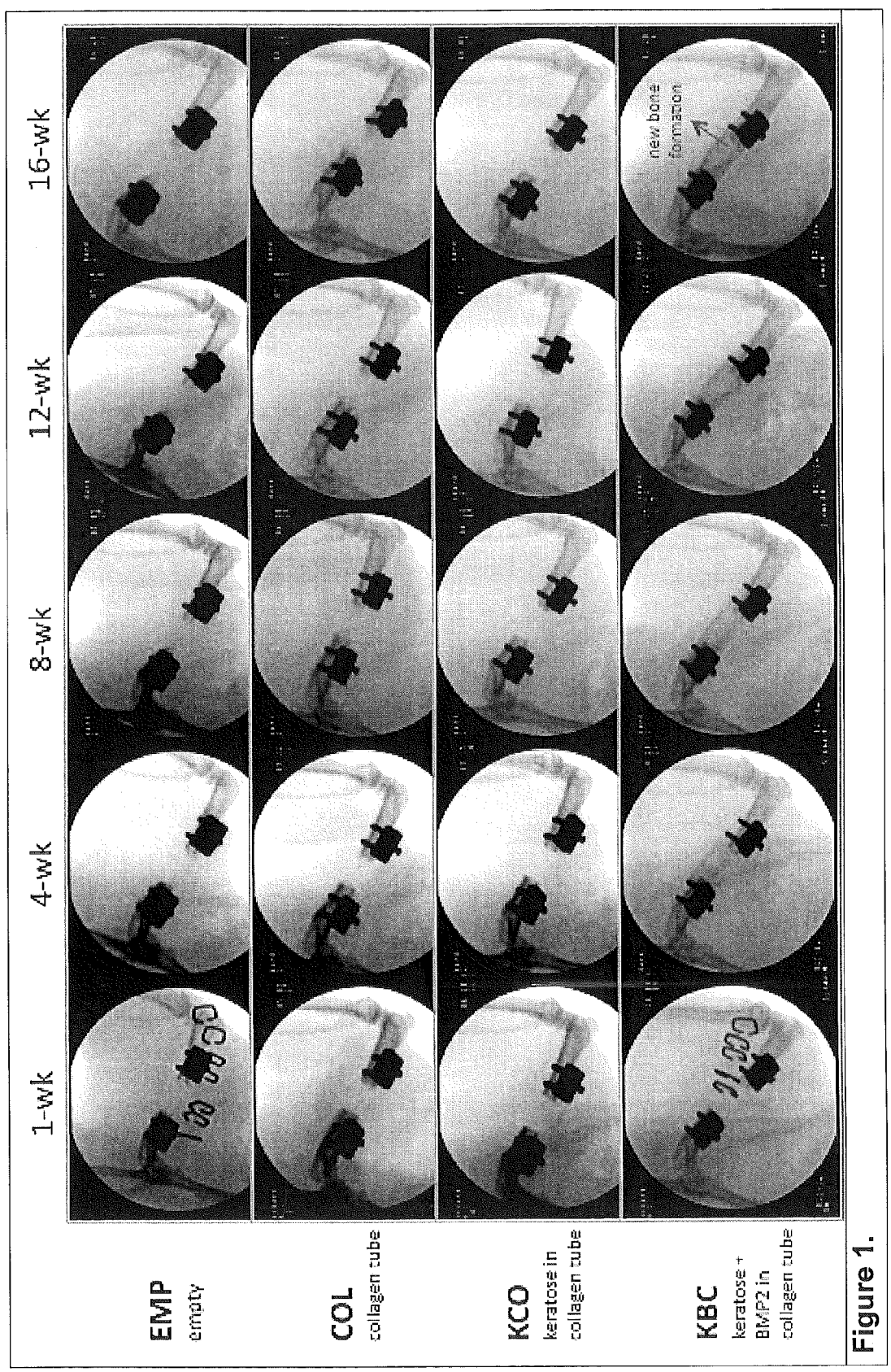
FIG. 1. Representative radiographic images showing the progression of bone healing in a rat femur defect model. The keratin with BMP2 shows bone bridging starting at 4 weeks and healing at 8 weeks.

Keratin compositions are provided that are useful for providing a matrix for cells to infiltrate, differentiate, and form tissue. Keratin containing implants can take the form of gels, coatings, fibers, or scaffolds. A preferred implant is a porous implant consisting of or consisting essentially of a keratin in the form of a nonwoven mesh, sponge, or hydrogel. Once stem or progenitor cells (endogenous and/or administered exogenous cells) infiltrate the implant and contact the keratin, gene expression changes are thought to occur that promote differentiation of the cells to form tissue. Alternatively, undifferentiated stem or progenitor cells can be mixed with the keratin composition (optionally also including differentiation factors) and placed into a tissue defect.

The disclosures of all cited United States Patent references are hereby incorporated by reference to the extent they are consistent with the disclosure herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" refers to and encompasses any and all possible combinations of one or more of the associated listed items, as well as the lack of combinations when interpreted in the alternative ("or").

Keratins are a family of proteins found in the hair, skin, and other tissues of vertebrates. Hair is a unique source of human keratins because it is one of the few human tissues that are readily available and inexpensive. Although other sources of keratins are acceptable feedstocks for the present invention, (e.g. wool, fur, horns, hooves, beaks, feathers, scales, and the like), human hair is preferred for use with human subjects because of its biocompatibility. The human hair can be end-cut, as one would typically find in a barber shop or salon.

"Keratin derivative" as used herein refers to any keratin fractionation, derivative, subfamily, etc., or mixtures thereof, alone or in combination with other keratin derivatives or other ingredients, including, but not limited to, alpha keratose, gamma keratose, alpha kerateine, gamma kerateine, meta keratin, keratin intermediate filaments, and combinations thereof, including the acidic and basic constituents thereof unless specified otherwise, along with variations thereof that will be apparent to persons skilled in the art in view of the present disclosure.

According to some embodiments, keratin compositions may include from 1 to 90% by weight of a keratin derivative, for example, from 1, 2, 5, 10, 15 or 20% to 40, 50, 60, or 70% or more by weight. In some embodiments, keratin compositions may include two or more keratin derivatives (e.g., a mixture of keratose and kerateine).

"Bone" as used herein includes any bone, such as: the pelvis; long bones such as the tibia, fibia, femur, humerus, radius, and ulna, ribs, sternum, clavicle, spinal bones (e.g., cervical or lumbar bones), etc.

"Fracture" or "break" as used herein with respect to bones includes any type thereof, including open or closed, simple or compound, comminuted fractures, compression fractures, hairline fractures, and fractures of any location including diaphyseal and metaphyseal. "Fracture" as used herein is also intended to include defects such as holes, gaps, spaces or openings, whether naturally occurring or surgically induced (e.g., by surgical removal of undesired tissue from bone).

Fractures may be of any bone, including but not limited to: ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones or metatarsal bones, etc. Indeed the compositions may be used for any suitable purpose for which bone graft or osteogenic implants are used, as described in U.S. Pat. No. 6,863,694 to Boyce et al.

"Antibiotic" as used herein includes any suitable antibiotic, including but not limited to cefazolin, vancomycin, gentamycin, erythromycin, bacitracin, neomycin, penicillin, polymycin B, tetracycline, biomycin, chloromycetin, streptomycin, ampicillin, azactam, tobramycin, clindamycin, gentamicin and combinations thereof. See, e.g., U.S. Pat. No. 6,696,073. In some embodiments the antibiotic is preferably a water soluble antibiotic.

"Particulate fillers" used to carry out the present invention can be formed from any suitable biocompatible material, such as a ceramic. In some embodiments, the particulate filler is preferably osteoconductive. Examples of suitable materials from which the filler may be formed include, but are not limited to, tetracalcium phosphate, tricalcium phosphate, calcium alkali phosphate ceramic, calcium phosphorus apatite, bioglass, calcium carbonate, calcium hydroxide, calcium oxide, calcium fluoride, calcium sulfate, magnesium hydroxide, hydroxyapatite, calcium phosphorus apatite, magnesium oxide, magnesium carbonate, magnesium fluoride, collagen, allograft bone, other resorbable biocompatible materials and mixtures thereof. See, e.g., U.S. Pat. Nos. 6,869,445; 5,281,265. In some embodiments, the particulate filler comprises hydroxyapatite, tricalcium phosphate, or a mixture thereof.

In some embodiments, particulate fillers may be included in the composition in a range of from 1 to 90% by weight, for example, from 1, 2, 5, 10, 15 or 20% to 40, 50, 60, or 70% or more by weight. In other embodiments, particular fillers are not included or are 0% by weight.

If included, the particulate filler content of the composition of the present invention may be in a range from about 0.1 percent to about 200 percent of the keratin content of the composition. In some embodiments, the particulate filler content of the composition may be in a range from about 10 percent to about 100 percent of the keratin content. In other embodiments of the invention, the particulate filler content of the composition may be in a range from about 20 percent to about 90 percent of the keratin content. In further embodiments, the particulate filler content may be in a range from about 40 percent to 80 percent of the keratin content. In additional embodiments, the particulate filler content of the composition may be in a range from about 25 percent to about 50 percent of the keratin content. As an example, in one embodiment, when the keratin concentration in 100 g of gel is 20 percent (i.e., 20 g keratin per 80 g water) then the particulate filler content may be in a range from about 2 g to about 20 g.

In particular embodiments, the composition of the present invention has a consistency similar to toothpaste or modeling clay. Further, in representative embodiments, the viscosity of the composition is fluid and malleable and able to hold a form or shape without a supporting structure.

"Cell" or "cells" are preferably mammalian cells (including mouse, rat, dog, cat, monkey and human cells), and in some embodiments human cells are preferred. "Isolated" as used herein signifies that the cells are placed into conditions other than their natural environment. Tissue or cells are "harvested" when initially isolated from a donor, e.g., a primary explant. "Cell culture" is the growth or proliferation of cells in vitro. Cells include, but are not limited to, stem and progenitor cells (e.g., embryonic, fetal, or adult), germ cells, somatic cells, cells strains or cell lines, etc., without limitation (See, e.g., U.S. Pat. No. 6,808,704 to Lanza et al.; U.S. Pat. No. 6,132,463 to Lee et al.; and US Patent Application Publication No. 2005/0124003 to Atala et al.). The cell donor may be of any age, including newborn, neonate, infant, child, adolescent, adult, and elderly.

Cells may be identified and/or categorized by methods known in the art, e.g., based upon properties that distinguish one cell type from another, e.g., density, size, shape, unique markers, unique metabolic pathways, nutritional requirements, protein expression, protein excretion, etc. Unique markers may be selected with fluorescent activated cell sorting (FACS), immunomagnetic bead sorting, magnetic activated cell sorting (MACS), panning, etc. Unique metabolic pathways and nutritional requirements may be assessed by varying the makeup and/or quantity of nutritional ingredients of the medium on which cells are grown, particularly in a serum-free environment. Protein expression and/or excretion may be detected with various assays, e.g., ELISA.

"Mesenchymal stem cells" or "MSC" as used herein refers to cells that are characterized by their ability to differentiate into bone, cartilage, or fat (i.e., adipose) cells. In some embodiments, MSC are plastic-adherent when maintained in standard culture conditions. In some embodiments, MSC express markers CD105, CD73 and CD90. In some embodiments, MSC lack expression of markers CD45, CD34, CD14 or CD11b, CD79a or CD19, and HLA-DR. See, e.g., Dominici et al., "Minimal criteria for defining multipotent mesenchymal stromal cells. The International Society for Cellular Therapy position statement," Cytotherapy (2006): 8(4): 315-317. Mesenchymal stem cells are normally found in and may be isolated from, e.g., adipose tissue or bone marrow, or from other tissues such as peripheral blood, blood vessel, skeletal muscle, skin, teeth, and gut.

"Bone marrow-derived stem cells" or "BMSC" are MSC harvested from bone marrow tissue. In some embodiments, BMSC include adherent marrow stromal cells.

"Adipose-derived stem cells" or "ADSC" are MSC harvested from adipose tissue. In some embodiments, ADSC express CD13, CD44, CD73, CD105, CD106, and/or vimentin. In some embodiments, ADSC are negative for the hematopoietic markers CD14 and CD45. ADSC may be collected from, e.g., adipose depots such as the abdominal superficial, the thigh, the abdominal deep, the arm, the thigh and the trochanteric depot.

"Bone cells" include those cells normally found in bone, and include osteoblasts, osteoclasts, osteocytes, and any combination thereof. Bone cells cultured using the processes described herein are useful for, among other things, implantation into a subject to treat bone fractures or defects, and/or promote bone healing.

"Cartilage cells" include those cells normally found in cartilage, which cells include chondrocytes. "Chondrocytes" produce and maintain the extracellular matrix of cartilage, by, e.g., producing collagen and proteoglycans. Cartilage is a highly specialized connective tissue found throughout the body, and its primary function is to provide structural support for surrounding tissues (e.g., in the ear and nose) or to cushion (e.g., in the trachea and articular joints). Types of cartilage include hyaline cartilage (articular joints, nose, trachea, intervertebral disks (NP), vertebral end plates), elastic cartilage (tendon insertion site, ligament insertion site, meniscus, intervertebral disks (AP)), costochondral cartilage (rib, growth plate), and fibrocartilage (ear). The loss of cartilage in a subject can be problematic, as it has a very limited repair capacity. Cartilage cells cultured using the processes described herein are useful for, among other things, implantation into a subject to treat cartilage injury or disease.

"Adipose cells" include those cells normally found in fat tissue (e.g., white fat tissue or brown fat tissue), which cells include adipocytes and preadipocytes.

"Peroxisome proliferator-activated receptor gamma" or "PPARγ" is considered a regulator of adipogenesis. High PPARγ expression favors differentiation of MSC to adipocytes. Conversely, PPARγ insufficiency favors differentiation of MSC to osteoblasts or chondrocytes. See Akune et al., J Clin Invest 2004; 113(6):846-55.

It has been shown that PPARγ expression naturally increases in MSC harvested from older donors (see Moerman et al., Aging Cell 2004; 3(6):379-89), thereby biasing these cells to form adipocytes rather than osteoblasts or chondrocytes, even when well-established differentiation protocols are used. Therefore, down-regulation of the expression of PPARγ may enhance the differentiation of stem and progenitor cells toward an osteogenic or a chondrogenic fate. Keratin biomaterials according to some embodiments can achieve this, and therefore can serve as adjuvants in the process of stem and progenitor cell differentiation, creating a more efficient production of the desired cell phenotype, in vitro or in vivo.

In some embodiments, osteocalcin expression upon MSC differentiation shows a fold-change of >1 as compared to an undifferentiated control, and preferably >2 or >5. In some embodiments, PPARγ expression in MSC is reduced to <1, <$\frac{1}{2}$, <$\frac{1}{20}$, as compared to an undifferentiated control.

Subjects are generally human subjects and include, but are not limited to, "patients." The subjects may be male or female and may be of any race or ethnicity, including, but not limited to, Caucasian, African-American, African, Asian, Hispanic, Indian, etc.

Subjects also include animal subjects, particularly mammalian subjects such as canines, felines, bovines, caprines, equines, ovines, porcines, rodents (e.g., rats and mice), lagomorphs, non-human primates, etc., for, e.g., veterinary medicine, laboratory research and/or pharmaceutical drug development purposes.

Subjects also may include osteoporotic patients. Osteoporosis is a disease of bones that leads to an increased risk of fracture. In osteoporosis the bone mineral density (BMD) is reduced, bone microarchitecture is deteriorating, and the amount and variety of proteins in bone is altered. The disease may be classified as primary type 1, primary type 2, or secondary. The form of osteoporosis most common in women after menopause is referred to as primary type 1 or postmenopausal osteoporosis. Primary type 2 osteoporosis or senile osteoporosis occurs after age 75 and is seen in both females and males at a ratio of 2:1. Finally, secondary osteoporosis may arise at any age and affects men and women equally. This form of osteoporosis results from chronic predisposing medical problems or disease, or prolonged use of medications such as glucocorticoids, when the disease is called steroid- or glucocorticoid-induced osteoporosis (SIOP or GIOP). Osteoporosis is often a component of the frailty syndrome.

"Treat" refers to any type of treatment that imparts a benefit to a patient, e.g., a patient having defect in a bone tissue, which may be due to injury, disease, etc. Treating includes actions taken and actions refrained from being taken for the purpose of improving the condition of the patient (e.g., the relief of one or more symptoms), delay in the onset or progression of the injury or disease, etc.

Treatment for a bone injury such as a fracture or nonunion, or for spinal bone fusion, may be performed by bone grafting, and may or may not include bone cells in the graft. Autologous bone cells may be obtained, for example, from the patient's bone tissue (e.g., from the pelvis, the iliac crest, the chin, the fibula, the ribs, the mandible, the skull, etc.). Allogeneic bone may also be used (e.g., from a cadaveric donor). In some embodiments, the bone tissue may be intermixed with the keratin-containing compositions taught herein.

A block graft may also be performed, in which a block of bone is placed whole into the area being grafted. In some embodiments, part of the periosteum and/or blood vessels may be harvested with the bone to be grafted (a vital bone graft). In some embodiments, the keratin-containing compositions taught herein may be provided in the space between the block of bone and the adjoining bone sections in the area to be treated.

Assessment of bone fracture or nonunion may be conducted as known in the art, e.g., x-ray. Assessment of bone density may be conducted as known in the art, e.g., dual energy x-ray absorptiometry, computer-assisted tomography and transmission ultrasound, etc. See US Patent Application Publication No. 2010/0113932. In some embodiments, and as desired, treatment may be ongoing until bone density or union is demonstrated, e.g., by x-ray or CT data, mineralization as defined by a >50, 60, 70, 80 or 90% normal mineral density, limb stability and load bearing as demonstrated by patient exam, etc.

With respect to the subject to be treated, cells may be syngeneic (i.e., genetically identical or closely related, so as to minimize tissue transplant rejection), allogeneic (i.e., from a non-genetically identical member of the same species) or xenogeneic (i.e., from a member of a different species). Syngeneic cells include those that are autogeneic (i.e., from the patient to be treated) and isogeneic (i.e., a genetically identical but different subject, e.g., from an identical twin). Cells may be obtained from a donor (either living or cadaveric) or derived from an established cell strain or cell line. For example, cells may be harvested from a donor (e.g., the potential recipient of the cells) using standard biopsy techniques known in the art.

In some embodiments, cells are harvested from a donor who is an adult at the time of harvest. As used herein, an "adult" means the donor is physically mature. An adult human, for example, according to some embodiments is at least 25, 30, 35, 40, 45, 50, or 55 years of age. The adult human donor according to some embodiments may also be older or elderly, for example, at least 60, 65, 70, 75, 80, 85 or 90 years of age at the time of harvest.

Proteins (such as growth factors) or other additives (such as differentiation factors, antibiotics, anti-inflammatories, and modulators of the immune response) may also be added to the cell and/or keratin preparations at any time. Also, various treatments may be applied to enhance adherence of cells to the substrate and/or to each other. Appropriate treatments are described, for example, in U.S. Pat. No. 5,613,982. For example, collagen, elastin, fibronectin, laminin, or proteoglycans may be included. As used herein, "growth factors" include molecules that promote the regeneration, growth and survival of cells or tissue. Growth factors that are used in some embodiments of the present invention may be those naturally found in keratin extracts, or may be in the form of an additive. The keratin or other substrate can also be impregnated with growth factors such as bone-derived growth factors, nerve growth factor (NGF), aFGF, bFGF, PDGF, TGFβ, VEGF, GDF-5/6/7, bone morphogenetic protein (e.g., BMP-1/2/3/4/5/6/7/8a/8b/10/13/12/14/15), IGF-1, etc., or these agents may be provided in a liquid carrier. In some embodiments, the growth factors (e.g., BMP2) may be provided at a concentration of from 0.001 to 1 mg/mL, or from 0.01 to 0.1 mg/mL.

In some embodiments, cells are provided in or further include a liquid carrier. The liquid carrier can be in the form of a suspension, solution, or any other suitable form, and may or may not include a keratin derivative as described herein. Examples of suitable liquid carriers include, but are not limited to, water, aqueous solutions (e.g., phosphate buffer solution, citrate buffer solution, etc.), liquid media (e.g., modified Eagle's medium ("MEM"), Hanks' Balanced Salts, etc.), gels (e.g., hydrogels), and so forth, and in some embodiments may include additional ingredients, as desired.

Preparation of Keratin Solutions and Substrates

One source of keratins is human hair, which may be endcut as one would typically find in a barbershop or salon, or purchased through commercial sources. It can be cleaned by washing in a warm water solution of mild detergent and freed of surface oils by washing with an organic solvent such as ethanol, ether, or acetone. A preferred solvent is ethanol.

Soluble keratins can be extracted from human hair fibers by oxidation or reduction using methods known in the art (see, for example, Rouse J G, Van Dyke M E. A review of keratin-based biomaterials for biomedical applications. Materials 2010; 3:999-1014). These methods typically employ a two-step process whereby the crosslinked structure of keratins is broken down by either oxidation or reduction. In these reactions, the disulfide bonds in cystine amino acid residues are cleaved, rendering the keratins soluble. In some embodiments, reactions cleave the disulfide bonds without appreciable disruption of amide bonds.

If one employs an oxidative treatment, the resulting keratins are referred to as "keratoses." If a reductive treatment is used, the resulting keratins are referred to as "kerateines" (See Scheme 1).

Scheme 1. General representations of (a) oxidation and (b) reduction of disulfide crosslinks in keratin. These reactions cleave the sulfur-sulfur bond in cystine residues, thereby destroying the superstructure and rendering the keratins soluble in the reaction media. The resultant fractions are keratose (a) and kerateine (b).

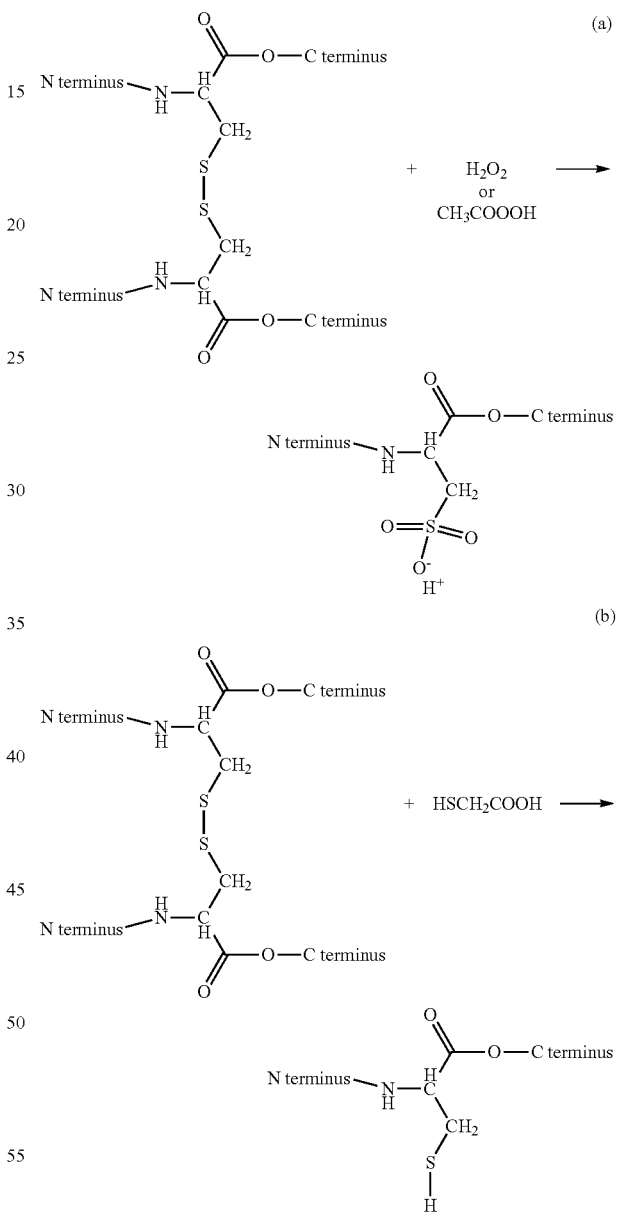

High molecular weight keratins, or "alpha keratins," (alpha helical), are thought to originate from the microfibrillar regions of the hair follicle, and typically range in molecular weight from about 40-85 kiloDaltons. Low molecular weight keratins, or "gamma keratins," or keratin-associated proteins (globular), are thought to originate from the matrix regions of the hair follicle, and typically range in molecular weight from about 3-30 kiloDaltons for KAP and 10-15 kiloDaltons for gamma keratins (see Rouse J G, Van Dyke M E. A review of keratin-based biomaterials for biomedical applications. Materials 2010; 3:999-1014).

Extracted keratin solutions are known to spontaneously self-assemble at the micron scale (see, e.g., Thomas et al., Int J Biol Macromol 1986; 8:258-64; van de Locht, Melliand Textilberichte 1987; 10:780-6). Self-assembly results in a highly regular structure with reproducible architectures, dimensionality, and porosity. When the keratin is processed correctly, this ability to self-assemble can be preserved and used to create regular architectures on a size scale conducive to cellular infiltration and/or attachment.

When keratins are hydrolyzed (e.g., with acids or bases), their molecular weight is reduced, and they lose the ability to self-assemble. Therefore, in some embodiments, processing conditions that minimize hydrolysis are preferred.

Many of the keratins can remain trapped within the cuticle's protective structure, so a second-step using a denaturing solution is typically employed to effect efficient extraction of the cortical proteins (alternatively, in the case of reduction reactions, these steps can be combined). This step may use solutions such as urea, transition metal hydroxides, surfactant solutions, and combinations thereof. Preferred methods are aqueous solutions of tris(hydroxymethyl)-aminomethane in concentrations between 0.1 and 1.0M, and urea solutions between 0.1 and 10M.

Crude (unfractionated) extracts of keratins, regardless of redox state, can be further refined into matrix (KAP and gamma), alpha, and/or charged (acidic or basic) fractions by a variety of methods such as isoelectric precipitation, dialysis, or high performance liquid chromatography (HPLC), as desired. In a crude extract, the alpha fraction begins to precipitate below pH 6 and is essentially completely precipitated by pH 4.2.

In some embodiments, KAP co-precipitate with the alpha fraction, thereby producing an alpha/KAP mixture. (see Rogers et al., "Human Hair Keratin-Associated Proteins (KAPs)," Int'l ref, cytol. 251:209-263 (2006)).

The gamma fraction remains in solution, but can be precipitated by addition of a non-solvent. Non-solvents are water miscible but do not dissolve keratins. A preferred non-solvent is an alcohol such as ethanol. Precipitation of the gamma fraction can be aided by cooling the ethanol and adding the keratin solution dropwise, rather than adding the ethanol to the keratin.

Keratose Production.

A preferred method for the production of keratoses is by oxidation with hydrogen peroxide, peracetic acid, or performic acid. A most preferred oxidant is peracetic acid. Preferred concentrations range from 1 to 10 weight/volume percent, the most preferred being approximately 2 w/v %. Those skilled in the art will recognize that slight modifications to the concentration can be made to affect varying degrees of oxidation, with concomitant alterations in reaction time, temperature, and liquid to solid ratio. It has also been discussed by Crewther et al. that performic acid offers the advantage of minimal peptide bond cleavage compared to peracetic acid. However, peracetic acid offers the advantages of cost and availability. A preferred oxidation temperature is between 0 and 100 degrees Celsius. A most preferred oxidation temperature is 37° C. A preferred oxidation time is between 0.5 and 24 hours. A most preferred oxidation time is 10 hours. A preferred liquid to solid ratio is from 5 to 100:1. A most preferred ratio is 20:1. After oxidation, the hair can be rinsed free of residual oxidant using a copious amounts of purified water.

The keratoses may be extracted from the oxidized hair using an aqueous solution of a denaturing agent. Protein denaturants are well known in the art, but preferred solutions include urea, transition metal hydroxides (e.g. sodium and potassium hydroxide), ammonium hydroxide, and tris(hydroxymethyl)aminomethane (Trizma® base). A preferred solution is Trizma base in the concentration range from 0.01 to 1M. A most preferred concentration is 0.1M. Those skilled in the art will recognize that slight modifications to the concentration can be made to effect varying degrees of extraction, with concomitant alterations in reaction time, temperature, and liquid to solid ratio. A preferred extraction temperature is between 0 and 100 degrees Celsius. A most preferred extraction temperature is 37° C. A preferred extraction time is between 0.5 and 24 hours. A most preferred extraction time is 2 hours. A preferred liquid to solid ratio is from 5 to 100:1. A most preferred ratio is 40:1. Additional yield can be achieved with subsequent extractions with dilute solutions of Trizma base or purified water. After extraction, the residual solids can be removed from solution by centrifugation and/or filtration.

Residual denaturing agent may be removed by dialysis against purified water or buffer solution. Concentration of the dialysis retentate may be followed by lyophilization or spray drying, resulting in a dry powder mixture of gamma and alpha keratoses as well as KAP. Alternately, an alpha/KAP mixture may be isolated from the crude extract solution by dropwise addition of acid until the pH of the solution reaches approximately 4.2. Preferred acids include sulfuric, hydrochloric, and acetic. A most preferred acid is concentrated hydrochloric acid. Precipitation of the alpha/KAP fraction begins at around pH 6.0 and continues until approximately 4.2. Fractional precipitation can be utilized to isolate different ranges of protein with different isoelectric properties. Precipitated alpha/KAP can be recovered by centrifugation, filtration, or the like. The alpha/KAP mixture is further purified by re-dissolving the solids in a denaturing solution. The same denaturing solutions as those utilized for extraction can be used. However, a preferred denaturing solution is Trizma base. Ethylene diamine tetraacetic acid (EDTA) can be added to complex and remove trace metals found in hair. A preferred denaturing solution is 100 mM tris base with 20 mM EDTA or DI water with 20 mM EDTA, if desired. If the presence of trace metals is not detrimental to the intended application, the EDTA step may be omitted. The alpha/KAP mixture can be re-precipitated from this solution by dropwise addition of hydrochloric acid to a final pH of 4.2. Isolation of the solid may be done by centrifugation, filtration or the like. This process can be repeated several times to further purify the alpha/KAP mixture, if desired, although significant destruction of amide bonds should be avoided according to some embodiments. In another preferred embodiment, the alpha/KAP fraction can be isolated from gamma-keratose by dialysis. Providing a high nominal low molecular weight cutoff membrane such that the gamma passes through the membrane and the alpha/KAP is retained can effect such separation. Preferred membranes are those having nominal low molecular weight cutoffs of 15,000 to 100,000 Da. Most preferred membranes are those having nominal low molecular weight cutoffs of 30,000 and 100,000 Da. The gamma keratose fraction can be isolated by addition to a water-miscible non-solvent.

Suitable non-solvents include ethanol, methanol, acetone, and the like. A most preferred non-solvent is ethanol. To effect precipitation, the gamma keratose solution can be concentrated by removal of excess water. This can be done using vacuum distillation, falling film evaporation, microfiltration, etc. After concentration, the gamma keratose solution is added dropwise to an excess of cold non-solvent. A most preferred method is to concentrate the gamma keratose solution to approximately 10 weight/volume (w/v) % protein and add it dropwise to an 8-fold excess of cold ethanol. The precipitated gamma keratose can be isolated by centrifugation or filtration and dried. Suitable methods for drying include freeze drying (lyophilization), air drying, vacuum drying, or spray drying. A most preferred method is freeze drying. Alternately, the gamma keratose can be isolated by dialysis against purified water or buffer solution. Preferred membranes for dialysis are those having nominal low molecular weight cutoffs between 1,000 and 5,000 Da. Most preferred membranes for dialysis are those having nominal low molecular weight cutoffs of 3,000 and 5,000 Da. This solution can be concentrated by additional dialysis and reduced to a dry powder by lyophilization or spray drying.

Several different approaches to further purification can be employed to keratose solutions (e.g., crude, alpha or gamma keratose). Care must be taken, however, to choose techniques that lend themselves to keratin's unique solubility characteristics. One of the most simple separation technologies is isoelectric precipitation. Another general method for separating keratins is by chromatography. Several types of chromatography can be employed to fractionate keratin solutions including size exclusion or gel filtration chromatography, affinity chromatography, isoelectric focusing, gel electrophoresis, ion exchange chromatography, and immunoaffinity chromatography. These techniques are well known in the art and are capable of separating compounds, including proteins, by the characteristics of molecular weight, chemical functionality, isoelectric point, charge, or interactions with specific antibodies, and can be used alone or in any combination to affect high degrees of separation and resulting purity.

A preferred purification method is ion exchange (IEx) chromatography. IEx chromatography is particularly suited to protein separation owning to the amphiphilic nature of proteins in general and keratins in particular. Depending on the starting pH of the solution, and the desired fraction slated for retention, either cationic or anionic IEx (CIEx or AIEx, respectively) techniques can be used. For example, at a pH of 7 and above, both gamma and alpha/KAP keratose fractions are soluble and above their isoelectric points. As such, they are anionic and can be bound to an anionic exchange resin. However, if the pH is below approximately 6, the alpha in the alpha/KAP fraction will not bind to the resin and instead passes through a column packed with such resin. A preferred solution for AIEx chromatography is alpha/KAP solution, isolated as described previously, in weak buffer solution at a concentration between 0 and 5 weight/volume %. A preferred concentration is approximately 2 w/v %. It is preferred to keep the ionic strength of said solution initially quite low to facilitate binding to the AIEx column. This is achieved by using a minimal amount of acid to titrate a purified water solution of the keratin to between pH 5.3 and 6. A most preferred pH is 5.3. This solution can be loaded onto an AIEx column such as DEAE-Sepharose or Q-Sepharose, or processed in bulk without the use of a column. The solution that passes through the column can be collected and further processed as described previously to isolate a fraction of alpha powder.

The basic fraction (including KAP) binds readily due to its lower isoelectric point, and can be washed off the column using salting techniques known in the art. A preferred elution medium is sodium chloride solution. A preferred concentration of sodium chloride is between 0.1 and 2M. A most preferred concentration is 2M. The pH of the solution is preferred to be between 6 and 12. A most preferred pH is 11. In order to maintain stable pH during the elution process, a buffer salt can be added. A preferred buffer salt is Trizma base. A preferred concentration of Trizma base is 100 mM. Those skilled in the art will recognize that slight modifications to the salt concentration and pH can be made to affect the elution of keratin fractions with differing properties. It is also possible to use different salt concentrations and pH's in sequence, or employ the use of salt and/or pH gradients to produce different fractions. Regardless of the approach taken, however, the column eluent can be collected and further processed as described previously to isolate purified fractions of alpha-keratose powders.

A complimentary procedure is also feasible using CIEx techniques. Namely, the alpha/KAP solution can be added to a cation exchange resin such as SP Sepharose (strongly cationic) or CM Sepharose (weakly cationic), and the basic (KAP) fraction collected with the pass through. The retained alpha fraction can be isolated by salting as previously described.

Kerateine Production.

Similar to the methods described above for extraction and purification of keratoses, kerateines can be produced by reduction of hair fibers with thioglycolic acid or beta-mercaptoethanol. A most preferred reductant is thioglycolic acid (TGA). Preferred concentrations range from 0.1 to 10M, the most preferred being approximately 1.0M or 0.5M. Those skilled in the art will recognize that slight modifications to the concentration can be made to effect varying degrees of reduction, with concomitant alterations in pH, reaction time, temperature, and liquid to solid ratio. A preferred pH is between 9 and 11. A most preferred pH is 10.2. The pH of the reduction solution is altered by addition of base. Preferred bases include transition metal hydroxides and ammonium hydroxide. A most preferred base is sodium hydroxide. The pH adjustment is affected by dropwise addition of a saturated solution of sodium hydroxide in water to the reductant solution. A preferred reduction temperature is between 0 and 100 degrees Celsius. A most preferred reduction temperature is 37° C. A preferred reduction time is between 0.5 and 24 hours. A most preferred reduction time is 12 hours. A preferred liquid to solid ratio is from 5 to 100:1. A most preferred ratio is 20:1. Unlike the previously described oxidation reaction, reduction is carried out at basic pH. That being the case, keratins are highly soluble in the reduction media and are expected to be extracted. The reduction solution may therefore be combined with the subsequent extraction solutions and processed accordingly.

Reduced keratins are not as hydrophilic as their oxidized counterparts. As such, reduced hair fibers will not swell and split open as will oxidized hair, resulting in relatively lower yields. Another factor affecting the kinetics of the reduction/extraction process is the relative solubility of kerateines. The relative solubility rankings in water, from most to least soluble, is gamma-keratose>alpha-keratose>gamma-kerateine>alpha-kerateine. Consequently, extraction yields from reduced hair fibers are not as high. This being the case, subsequent extractions may be conducted with additional reductant plus denaturing agent solutions. Typical solutions for subsequent extractions include TGA plus urea, TGA plus Trizma base, or TGA plus sodium hydroxide. After extraction, crude fractions of alpha/KAP and gamma kerateine can be isolated using the procedures described for keratoses. However, precipitates of gamma and alpha/KAP kerateine re-form their cystine crosslinks upon exposure to oxygen. Precipitates should, therefore, preferably be re-dissolved quickly so as to avoid insolubility during the purification stages, or precipitated in the absence of oxygen.

Purification of kerateine solutions can be conducted similar to those described for keratoses. Those skilled in the art will recognize that the chemical nature of kerateines varies from that of keratoses, primarily in the fate of pendant sulfur groups that will alter chemical properties such as isoelectric points. As such, modifications in the conditions for separation techniques such as ion exchange chromatography are needed for optimization.

All forms of keratin (crude mixtures as well as fractionated materials) have demonstrated an interesting and unexpected ability to change the expression of certain genes in differentiating MSC. Using these different keratins, MSC from a variety of tissues can be exposed to the biomaterial in different forms in both culture systems and in vivo. Different stem and progenitor cells can be used depending on the desired application.

Keratin can be added to the media and the cells seeded onto coated or uncoated cultureware. Alternatively, keratins can be coated onto cell cultureware such as polystyrene dishes or flasks using techniques known in the art. For example, incubation of the cultureware with a dilute solution of keratin can be used. If better adhesion of the coating is desired, a silane coupling agent can be used. Alternatively, thin gel coatings of keratin can be used to provide a three-dimensional matrix to the cells. MSC can then be seeded onto the keratin substrate and subjected to the differentiation protocol.

Differentiation protocols are known in the art. See, e.g., Jaiswal N, Haynesworth S E, Caplan A I, Bruder S P J. Osteogenic differentiation of purified, culture-expanded human mesenchymal stem cells in vitro. Cell Biochem 1997; 64(2):295-312 for osteogenesis; Mackay A M, Beck S C, Murphy J M, Barry F P, Chichester C O, Pittenger M F. Chondrogenic differentiation of cultured human mesenchymal stem cells from marrow. Tissue Eng 1998; 4(4):415-28 for chondrogenesis.

In some embodiments, the keratin derivative comprises, consists or consists essentially of a particular fraction or subfraction of keratin. The derivative in some embodiments may comprise, consist or consist essentially of at least 80, 90, 95 or 99 percent by weight of said fraction or subfraction (or more).

In some embodiments, the keratin derivative comprises, consists of, or consists essentially of acidic and/or basic, alpha and/or gamma keratose, where the keratose comprises, consists of or consists essentially of at least 80, 90, 95 or 99 percent by weight of acidic and/or basic, alpha and/or gamma keratose (or more).

In some embodiments, the keratin derivative comprises, consists of, or consists essentially of acidic and/or basic, alpha and/or gamma keratose, where the keratose comprises, consists of, or consists essentially of at least 80, 90, 95 or 99 percent by weight of acidic and/or basic, alpha and/or gamma keratose (or more). In other embodiments, the keratin derivative comprises, consists of or consists essentially of alpha/KAP keratose, where the keratose comprises, consist of or consists essentially of at least 80, 90, 95 or 99 percent by weight of alpha/KAP keratose (or more).

In some embodiments, the keratin derivative comprises, consists of, or consists essentially of acidic and/or basic, alpha and/or gamma kerateine, where the kerateine comprises, consists of or consists essentially of at least 80, 90, 95 or 99 percent by weight of acidic and/or basic, alpha and/or gamma kerateine (or more). In other embodiments, the keratin derivative comprises, consists of, or consists essentially of alpha/KAP kerateine, where the kerateine comprises, consist of, or consists essentially of at least 80, 90, 95 or 99 percent by weight of alpha/KAP keratose (or more).

The basic alpha keratose is preferably produced by separating basic alpha keratose from a mixture comprising acidic and basic alpha keratose, e.g., by ion exchange chromatography, and optionally the basic alpha keratose has an average molecular weight of from 10 to 100 or 200 kiloDaltons. More preferably, the average molecular weight is from 30 or 40 to 90 or 100 kiloDaltons. Optionally, but in some embodiments preferably, the process further comprises the steps of re-dissolving said basic alpha-keratose in a denaturing and/or buffering solution, optionally in the presence of a chelating agent to complex trace metals, and then re-precipitating the basic alpha keratose from the denaturing solution. It will be appreciated that the composition preferably contains not more than 5, 2, 1, or 0.1 percent by weight of acidic alpha keratose, or less.

The acidic alpha keratose may be produced by a reciprocal of the foregoing technique: that is, by separating and retaining acidic alpha keratose from a mixture of acidic and basic alpha keratose, e.g., by ion exchange chromatography, and optionally the acidic alpha keratose has an average molecular weight of from 10 to 100, 120, 150, 200, 250 or 500 kiloDaltons. More preferably, the average molecular weight is from 30 or 40 to 90, 100, 120, 150, 200, 250 or 500 kiloDaltons. Optionally, but in some embodiments preferably, the process further comprises the steps of re-dissolving said acidic alpha-keratose in a denaturing solution and/or buffering solution, optionally in the presence of a chelating agent to complex trace metals, and then re-precipitating the basic alpha keratose from the denaturing solution. It will be appreciated that the composition preferably contains not more than 5, 2, 1, or 0.1 percent by weight of basic alpha keratose, or less.

Basic and acidic fractions of other keratoses (e.g., KAP and gamma keratose) can be prepared in like manner as described above for basic and acidic alpha keratose.

Basic alpha kerateine is preferably produced by separating basic alpha kerateine from a mixture of acidic and basic alpha kerateine, e.g., by ion exchange chromatography, and optionally the basic alpha kerateine has an average molecular weight of from 10 to 100, 120, 150, 200, 250 or 500 kiloDaltons. More preferably, the average molecular weight is from 30 or 40 to 90, 100, 120, 150, 200, 250 or 500 kiloDaltons. Optionally, but preferably, the process further includes the steps of re-dissolving said basic alpha-kerateine in a denaturing and/or buffering solution, optionally in the presence of a chelating agent to complex trace metals, and then re-precipitating the basic alpha kerateine from the denaturing solution. It will be appreciated by those of skill in the art that the composition preferably contains not more than 5, 2, 1, or 0.1 percent by weight of acidic alpha kerateine, or less.

The acidic alpha kerateine may be produced by a reciprocal of the foregoing technique; that is, by separating and retaining acidic alpha kerateine from a mixture of acidic and basic alpha kerateine, e.g., by ion exchange chromatography, and optionally the acidic alpha kerateine has an average molecular weight of from 10 to 100, 120, 150, 200, 250 or 500 kiloDaltons. More preferably, the average molecular weight is from 30 or 40 to 90, 100, 120, 150, 200, 250 or 500 kiloDaltons. Optionally, but preferably, the process further comprises the steps of re-dissolving said acidic alpha-kerateine in a denaturing and/or buffering solution), optionally in the presence of a chelating agent to complex trace metals, and then re-precipitating the basic alpha kerateine from the denaturing solution. It will be appreciated that the composition preferably contains not more than 5, 2, 1, or 0.1 percent by weight of basic alpha kerateine, or less.

Basic and acidic fractions of other kerateines (e.g., KAP and gamma kerateine) can be prepared in like manner as described above for basic and acidic alpha kerateine. Gamma keratins are typically precipitated in a non-solvent such as ethanol.

As used herein, "acidic" keratins are those keratins that are protonated at a predetermined pH such that they carry a net positive charge; "basic" keratins are those keratins that are de-protonated at a predetermined pH such that they carry a net negative charge. The Keratin Associated Proteins (KAP) as used herein carry a negative charge at the predetermined pH and bind to an anionic exchange resin, and thus in some embodiments is included in the basic keratin fractions taught herein. In some embodiments, the predetermined pH is between 5 and 7. In some embodiments, the pH is 6. For example, in some embodiments, keratose or kerateine is separated into acidic and basic fractions (e.g., by ion exchange chromatography) performed at a solution pH of 6, with the resulting acidic fraction including those keratins having a net positive charge at pH 6, and the basic fraction including those keratins having a net negative charge at pH 6. Likewise, for separation at a predetermined pH of 5.3, the acidic fraction will include those keratins having a net positive charge at pH 5.3 and the basic fraction will include those keratins having a net negative charge at pH 5.3.

Those skilled in the art will recognize that the predetermined pH is selected to effect the best separation between acidic and basic proteins based upon their isoelectric points (see, e.g., Table 1), though solubility at that pH should also be considered. When the pH of the solution is between the isoelectric point of these acidic and basic keratin fractions, basic keratin proteins will be de-protonated to have a net negative charge and bind to an anionic media (e.g., DEAE-Sepharose or Q-Sepharose (anion exchange)), while the acidic proteins will be protonated to have a net positive charge and pass through the column, thereby effecting separation.

Further discussion of keratin preparations are found in U.S. Patent Application Publication 2009/0004242 (Van Dyke), which is incorporated by reference herein in its entirety.

Formulations.

Dry powders may be formed of keratin preparations as described above in accordance with known techniques such as freeze drying (lyophilization). In some embodiments, compositions of the invention may be produced by mixing such a dry powder composition form with an aqueous solution to produce a composition having an electrolyte solution with a keratin solubilized therein. The mixing step can be carried out at any suitable temperature, typically room temperature, and can be carried out by any suitable technique such as stirring, shaking, agitation, etc. The salts and other constituent ingredients of the electrolyte solution (e.g., all ingredients except the keratin derivative and the water) may be contained entirely in the dry powder, entirely within the aqueous composition, or may be distributed between the dry powder and the aqueous composition. For example, in some embodiments, at least a portion of the constituents of the electrolyte solution is contained in the dry powder.

In use, the compositions may be rehydrated if necessary, and used to treat fractures in a subject (e.g., filling bone defects) in accordance with known techniques by contacting the composition to the fracture in a treatment-effective amount.

The formation of a composition including keratin materials such as described above can be carried out in accordance with techniques long established in the field or variations thereof that will be apparent to those skilled in the art. In some embodiments, the keratin preparation is dried and rehydrated prior to use. See, e.g., U.S. Pat. No. 2,413,983 to Lustig et al., U.S. Pat. No. 2,236,921 to Schollkipf et al., and U.S. Pat. No. 3,464,825 to Anker. In some embodiments, lyophilized material is rehydrated with a suitable solvent, such as water or phosphate buffered saline (PBS). The material can be sterilized, e.g., by $\gamma$-irradiation (800 krad) using a $^{60}Co$ source. Other suitable methods of forming keratin matrices include, but are not limited to, those found in U.S. Pat. No. 6,270,793 (Van Dyke et al.), U.S. Pat. No. 6,274,155 (Van Dyke et al.), U.S. Pat. No. 6,316,598 (Van Dyke et al.), U.S. Pat. No. 6,461,628 (Blanchard et al.), U.S. Pat. No. 6,544,548 (Siller-Jackson et al.), and U.S. Pat. No. 7,01,987 (Van Dyke).

In some embodiments, keratin-containing compositions are sterile filtered and processed aseptically, or terminally sterilized using ethylene oxide, e-beam, gamma, or other low temperature method (i.e. <50° C.).

The composition may be aseptically packaged in a suitable container, such as a flexible polymeric bag or bottle, or a foil container, or may be provided as a kit of sterile dry powder in one container and sterile aqueous solution in a separate container for mixing just prior to use. When provided packaged in a sterile container, in some embodiments the composition preferably has a shelf life of at least 4 or 6 months (up to 2 or 3 years or more) at room temperature, prior to substantial loss of viscosity (e.g., more than 10 or 20 percent) and/or structural integrity of the keratin composition.

The composition may be provided in a precursor solution. For example, keratin containing precursor solution can be provided in a glass ampule ready to use directly or after dilution by the user. In the case of kerateine compositions, which can re-crosslink in the presence of oxygen in air, a sterile precursor solution in a sealed ampule under an inert atmosphere (e.g., nitrogen) can be provided.

In further embodiments, if desired or necessary, the subject may be administered an agent for inhibiting transplant rejection of the administered cells, such as rapamycin, azathioprine, corticosteroids, cyclosporin and/or FK506, in accordance with known techniques. See, e.g., R. Calne, U.S. Pat. Nos. 5,461,058, 5,403,833 and 5,100,899; see also U.S. Pat. Nos. 6,455,518, 6,346,243 and 5,321,043. Some embodiments use a combination of implantation and immunosuppression, which minimizes rejection.

Mixtures of Keratose and Kerateine.

In some embodiments, mixtures of keratose and kerateine are provided. Because kerateine is absorbed more slowly than keratose in the body, providing a mixture of the two may be useful in controlling the absorption rate in vivo. Preferred ratios according to some embodiments range from 1:10 to 10:1 keratose:kerateine, with most preferred ranging from 1:10 or 1:5 to 1:1 keratose:kerateine.

In some embodiments, mixtures of keratose and kerateine comprise acidic or basic alpha keratose mixed with acidic or basic alpha kerateine. In other embodiments, mixtures of keratose and kerateine may comprise gamma keratose and/or gamma kerateine. In such embodiments, the gamma keratose/kerateine may be up to 20% of the keratin composition. In other embodiments, the gamma keratose/kerateine may be 1, 2, 3, 4, 5, 6, 7, 8, 9, 10, 11, 12, 13, 14, 15, 16, 17, 18, or 19% of the keratin composition.

The present invention is explained in greater detail in the following non-limiting Examples.

EXPERIMENTAL

Example 1

Crude preparations of keratins (oxidized and reduced forms, keratoses and kerateines, respectively) were obtained from human hair. They were then made into gels and lyophilized scaffolds following incorporation of bone morphogenetic protein 2 (BMP2). Gels were prepared at 10 and 20 weight percent for kerateine and keratose, respectively, and contained 1.0 mg of BMP2 per 1 mL of gel.

Constructs were fabricated by placing the biomaterials in the lumen of collagen 1 tubes, and they were implanted in an 8-mm critical-size rat femur defect. Assessment of bone regeneration was conducted via fluoroscopy, micro-computed tomography (μ-CT), dual energy X-ray absorptiometry (DEXA), torsional testing, and histological staining analyses.

Figure 2:
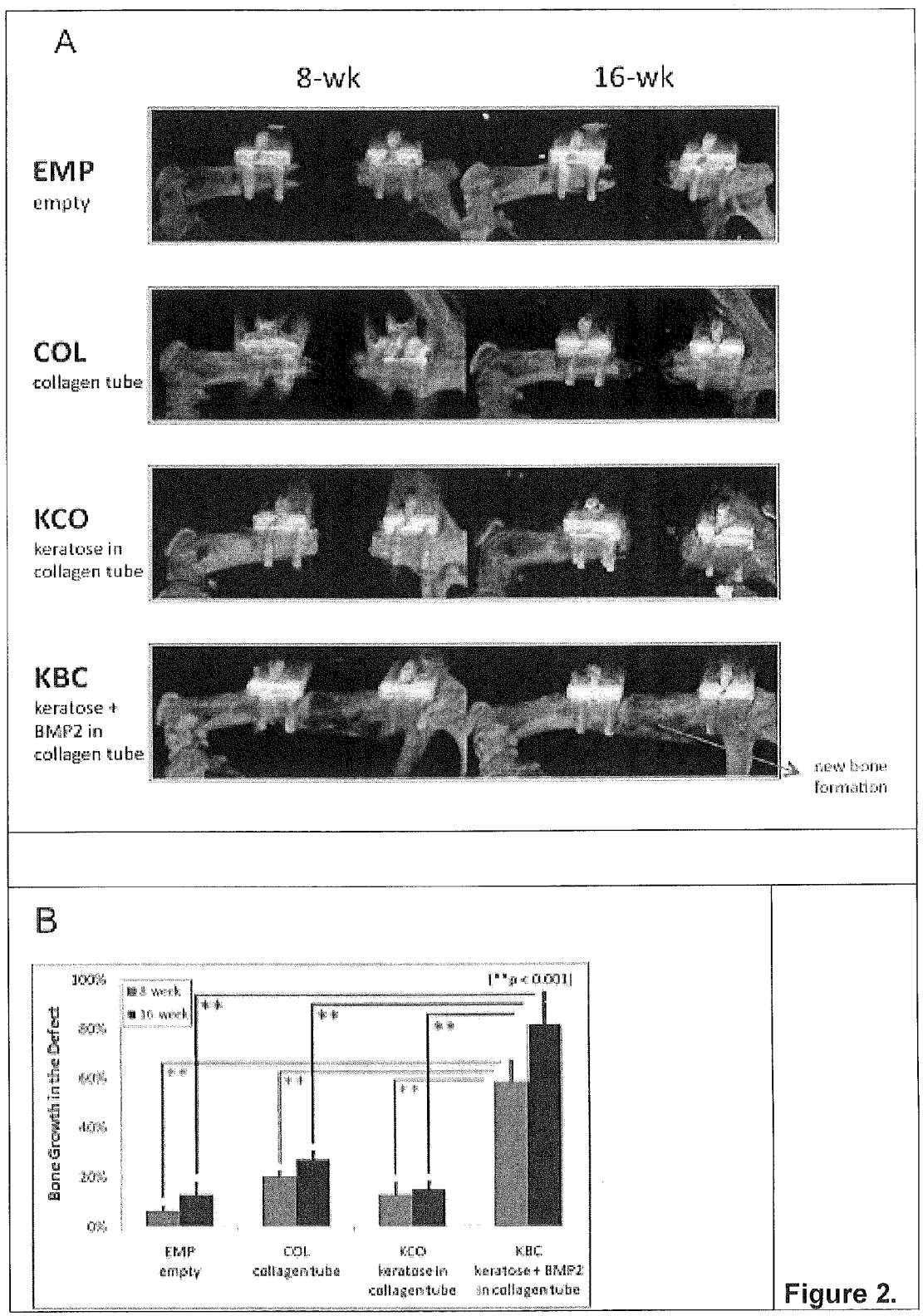
FIG. 2. Representative micro-CT images of rat femurs (A). The keratin with BMP2 shows complete healing by the 16 week time point. Quantification of these images shows a significant difference in the amount of bone formed in the keratin plus BMP2 treatment group (B).
Figure 3:
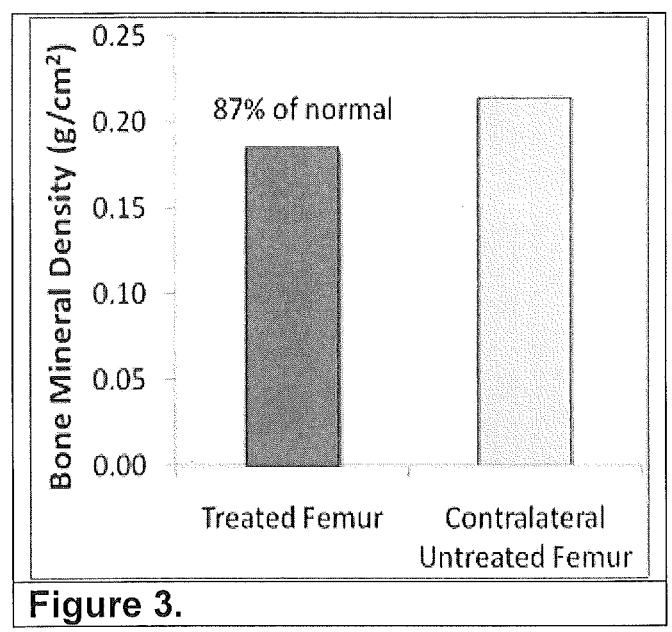
FIG. 3. Bone density scan data. Bone mineral density as determined by DEXA shows keratin with BMP had a nearly normal value by 16 weeks.
Figure 4:
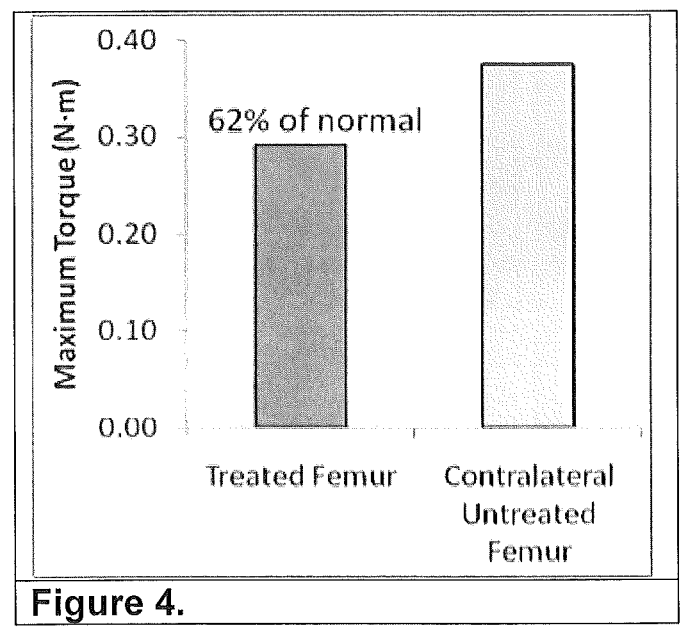
FIG. 4. Strength of retrieved femurs after 16 weeks as determine by torsional biomechanical testing. These data suggest that the keratin plus BMP treated femurs recovered more than half of their original strength.

BMP2-loaded keratose and kerateine constructs were able to regenerate new bone tissues that fully bridge the critical-size defect after 16 weeks in vivo (FIG. 1). The deposited bone amounts in the gap site based on μ-CT were statistically greater than those in the controls (empty and keratose only) at the 8 and 16-week time points (FIG. 2). DEXA scans yielded ~86% mineralization compared to normal bone (FIG. 3) and biomechanical tests generated torque values close to pre-injured states (FIG. 4). Collagen matrices, osteoblasts, and osteocytes were observed within the bone regenerates.

Keratins with osteoinductive BMP2 within a collagen tube demonstrated regenerative responses approaching the mineral density, biomechanical properties, and cellular composition of normal bone. This system may form the basis of a strategy which can effectively bridge critical size defects (i.e., defects that do not spontaneously heal and result in a non-union) with functional bone tissue.

Example 2

Culture of Mesenchymal Stem Cells on Kerateine Substrates

Keratins are intermediate filament cytoskeletal proteins that form stable network structures, and thus have the potential to be used as substrates for cell attachment in the development of tissue-engineered constructs. Adult mesenchymal stem cells (MSCs) derived from bone marrow (BM-MSCs) and adipose tissue (AD-MSCs) are commonly employed for biomaterial seeding since they have the capability to differentiate into multiple connective tissues including bone and adipose to replace the targeted damaged structure.

The reduced form of keratins called kerateines can assemble through disulfide bonding and such assembled kerateines can support a variety of cells, particularly those with fibroblast morphologies. It is therefore thought that the fibroblastic MSCs can attach and thrive on kerateines.

To test the hypothesis, BM-MSCs and AD-MSCs were first seeded on kerateine coating (K2D) and kerateine thin gel/film (K3D). Coatings were produced by incubating culture plates in a dilute solution of kerateine overnight, aspirating the excess solution, and rinsing the coating with buffer solution prior to cell seeding. Thin films were prepared by pipetting a 4 weight percent solution of kerateine into tissue culture plates and allowing the material to crosslink by overnight exposure to air (with a lid on the plate) at 37 degrees C. The gels were conditioned with cell media prior to seeding. BM-MSCs and AD-MSCs were also seeded on control surfaces including uncoated plasma-treated tissue culture plastic (UNC), gelatin coating (GEL), and Matrigel™ coating (BD Biosciences) (MAT). Cell behavior (attachment, viability, and proliferation) on the five different substrates were quantified. Attachment ratios were obtained by the number of adhered cells after 6 h of incubation divided by the total number of seeded cells. Cell viabilities were measured using Live/Dead® microscopy assay (Invitrogen). Cell proliferation results determined by growth curves and doubling times were obtained by treating the cells with the MTS reagent at multiple time points over a 1-week span. MSCs were also assessed for their surface markers (+CD29, 44, 73, 90, 105; −CD14, 34, 45) at different passages using flow cytometry. MSCs were differentiated for osteogenesis (+dexamethasone, vitamin C, and glycerol-2-phosphate) and adipogenesis (+dexamethasone, IBMX, indomethacin, and insulin) for 3 weeks and subsequently stained using Alizarin Red S and Oil Red O, respectively. The stained images were quantified and normalized against the number of cells (DAPI staining). Finally, using quantitative real-time PCR (qRT-PCR), osteogenic (osteocalcin and RUNX2) and adipogenic (PPARγ and lipoprotein lipase) gene expressions were evaluated. Undifferentiated cells were used as controls for both staining and PCR experiments.

Figure 5:
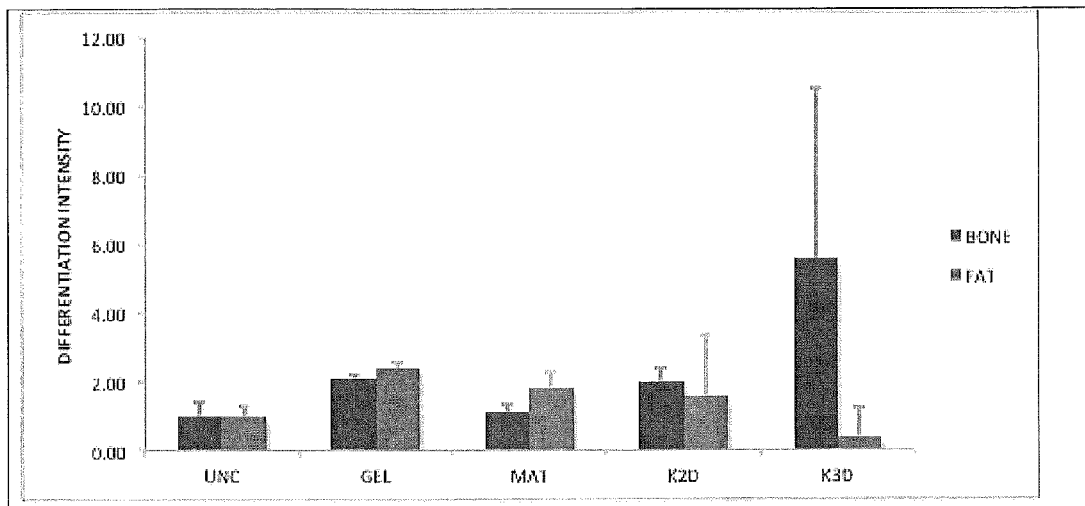
FIG. 5. Bone marrow derived MSC differentiation on keratin and control substrates.
Figure 6:
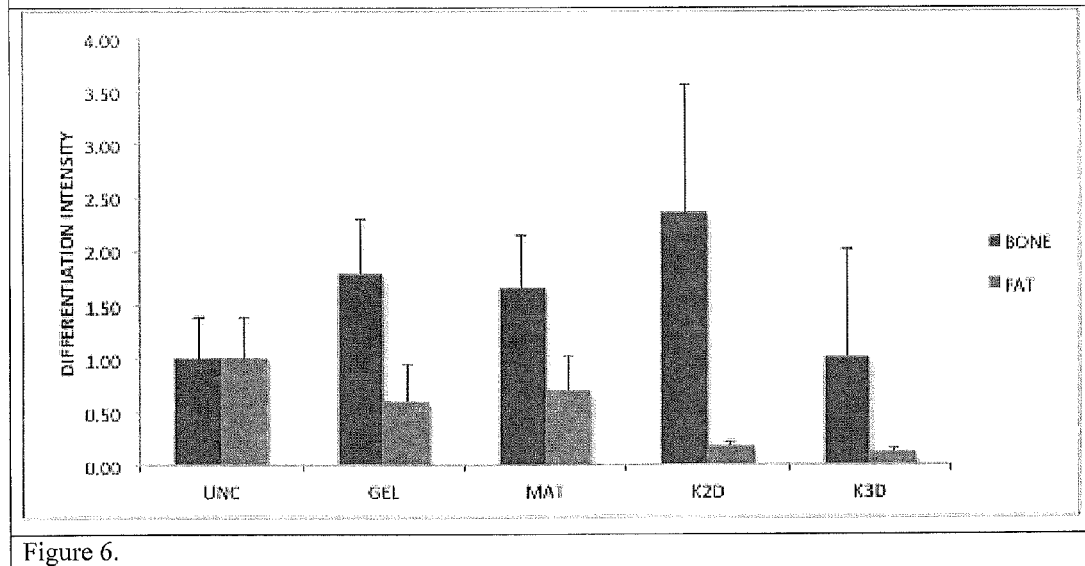
FIG. 6. Adipose derived MSC differentiation on keratin and control substrates.

Kerateine substrates (K2D and K3D) (alpha+KAP, dialyzed using a 100 kDa low molecular weight cutoff membrane) as wells as the controls (untreated or "UNC", gelatin or "GEL", and Matrigel® "MAT") were able to support initial adhesion of cells at ≥94%. After the attachment, MSCs from both adipose tissue and bone marrow remained highly viable over time. They proliferated on all surfaces with doubling time ranging from 2.5-3.5 days. Kerateine substrates generally allowed a slower rate of proliferation compared to the controls, and it was found that growth on K2D>K3D. Kerateine films with softer consistency (at 4 weight percent) also provided less cell growth. Positive and negative stem cell-surface markers were retained on cells on kerateines. Under differentiation conditions (i.e., use of osteogenic and adipogenic induction media), BM-MSCs on kerateine substrates appeared to induce higher osteogenic differentiation but fewer adipocytes when induced with the adipogenic media. The differentiation capacities on UNC, GEL, and MAT all appear similar compared to the UNC control (FIG. 5). AD-MSCs generally differentiate into osteoblasts more on GEL, MAT, K2D, and K3D than UNC. However, for adipogenic differentiation only the kerateine substrates provided a down regulatory response compared to the uncoated control (FIG. 6). qRT-PCR is performed to confirm the staining in which the kerateine substrates provided less capacity to differentiate into adipocytes.

Results from this study support the use of kerateine biomaterial for bone regeneration to drive the repair stem cells towards the osteogenic lineage and avoid the adipogenic route.

The foregoing is illustrative of the present invention, and is not to be construed as limiting thereof. The invention is defined by the following claims, with equivalents of the claims to be included therein.

That which is claimed is:

1. A bone graft composition, comprising:
    (a) from 1 to 90 percent by weight keratose;
    (b) from 1 to 90 percent by weight kerateine;
    (c) from 0.001 to 5 percent by weight bone morphogenetic protein 2 (BMP2);
    (d) optionally, from 1 to 90 percent by weight particulate filler;
    (e) optionally, from 0.001 to 5 percent by weight antibiotic; and
    (f) water or saline to balance.

2. The composition of claim 1, wherein said composition is a nonwoven mesh, sponge, or hydrogel.

3. The composition of claim 1, wherein said composition is sterile.

4. The composition of claim 3 packaged in a sterile container.

5. The composition of claim 1, wherein said keratose is alpha/KAP keratose, gamma keratose, or mixtures thereof.

6. The composition of claim 1, wherein said kerateine is alpha/KAP kerateine, gamma kerateine, or mixtures thereof.

7. The composition of claim 1, wherein said composition comprises from 10 to 90 percent by weight keratose and from 90 to 10 percent by weight kerateine.

8. The composition of claim 1, wherein said composition comprises from 1 to 30 percent by weight keratose and from 1 to 30 percent by weight kerateine.

9. A lyophilized or freeze-dried composition which upon reconstitution with water or saline solution produces a bone graft material composition, comprising:
  (a) from 1 to 90 percent by weight keratose;
  (b) from 1 to 90 percent by weight kerateine;
  (c) from 0.001 to 5 percent by weight bone morphogenetic protein 2 (BMP2);
  (d) optionally, from 1 to 90 percent by weight particulate filler;
  (e) optionally, from 0.001 to 5 percent by weight antibiotic; and
  (f) water or saline to balance.

10. A bone graft composition, comprising:
  (a) from 1 to 90 percent by weight keratose;
  (b) from 1 to 90 percent by weight kerateine;
  (c) from 1 to 90 percent by weight particulate filler;
  (d) optionally, from 0.001 to 5 percent by weight antibiotic; and
  (e) water or saline to balance,
  wherein said particulate filler is selected from the group consisting of tetracalcium phosphate, tricalcium phosphate, calcium alkali phosphate ceramic, bioglass, calcium carbonate, calcium hydroxide, calcium oxide, calcium fluoride, calcium sulfate, magnesium hydroxide, hydroxyapatite, calcium phosphorus apatite, magnesium oxide, magnesium carbonate, magnesium fluoride, collagen, and mixtures thereof.

11. The composition of claim 10, wherein said particulate filler is selected from the group consisting of hydroxyapatite, tricalcium phosphate, and mixtures thereof.

12. The composition of claim 10, wherein said composition comprises an antibiotic selected from the group consisting of cefazolin, vancomycin, gentamycin, erythromycin, bacitracin, neomycin, penicillin, polymycin B, tetracycline, biomycin, chloromycetin, streptomycin, ampicillin, azactam, tobramycin, clindamycin, gentamicin, and combinations thereof.

13. A bone graft composition, comprising:
  (a) from 1 to 90 percent by weight keratose;
  (b) from 1 to 90 percent by weight kerateine;
  (c) optionally, from 1 to 90 percent by weight particulate filler;
  (d) optionally, from 0.001 to 5 percent by weight antibiotic; and
  (e) water or saline to balance, and
  further comprising stem cells.

14. The composition of claim 13, wherein said stem cells are mesenchymal stem cells.

15. The composition of claim 14, wherein said mesenchymal stem cells are harvested from bone marrow or adipose tissue.

16. The composition of claim 13, wherein said stem cells are adipose derived stem cells.

17. The composition of claim 13, wherein said stem cells are collected from a human subject who is at least 40 years old at the time of harvest.

18. A method of treating a bone deficiency in a subject in need thereof, comprising administering to said subject in a treatment effective amount a bone graft composition, comprising:
  (a) from 1 to 90 percent by weight keratose;
  (b) from 1 to 90 percent by weight kerateine;
  (c) optionally, from 1 to 90 percent by weight particulate filler;
  (d) optionally, from 0.001 to 5 percent by weight antibiotic; and
  (e) water or saline to balance.

19. The method of claim 18, wherein said subject is an osteoporotic or osteopenic subject.

20. The method of claim 18, wherein said administering comprises injecting.

21. The method of claim 18, wherein the bone graft composition further comprises autologous stem cells.

22. The method of claim 21, wherein said stem cells are mesenchymal stem cells.

23. The method of claim 22, wherein said mesenchymal stem cells are harvested from bone marrow or adipose tissue.

24. The method of claim 21, wherein said stem cells are adipose derived stem cells.

25. The method of claim 21, wherein said stem cells are collected from a human subject who is at least 40 years old at the time of harvest.

26. A method of treating a fracture in a subject in need thereof, comprising contacting to said fracture in a treatment-effective amount a bone graft composition, comprising:
  (a) from 1 to 90 percent by weight keratose;
  (b) from 1 to 90 percent by weight kerateine;
  (c) optionally, from 1 to 90 percent by weight particulate filler;
  (d) optionally, from 0.001 to 5 percent by weight antibiotic; and
  (e) water or saline to balance.

27. The method of claim 26, wherein said composition further comprises from 0.001 to 5 percent by weight bone morphogenetic protein 2 (BMP2).

28. The method of claim 26, wherein said composition comprises a particulate filler selected from the group consisting of tetracalcium phosphate, tricalcium phosphate, calcium alkali phosphate ceramic, bioglass, calcium carbonate, calcium hydroxide, calcium oxide, calcium fluoride, calcium sulfate, magnesium hydroxide, hydroxyapatite, calcium phosphorus apatite, magnesium oxide, magnesium carbonate, magnesium fluoride, collagen, and mixtures thereof.

29. The method of claim 26, wherein said composition comprises a particulate filler selected from the group consisting of hydroxyapatite, tricalcium phosphate, and mixtures thereof.

30. The method of claim 26, wherein said composition comprises an antibiotic selected from the group consisting of cefazolin, vancomycin, gentamycin, erythromycin, bacitracin, neomycin, penicillin, polymycin B, tetracycline, biomycin, chloromycetin, streptomycin, ampicillin, azactam, tobramycin, clindamycin, gentamicin, and combinations thereof.

* * * * *